(12) United States Patent
Palmer et al.

(10) Patent No.: US 7,297,125 B2
(45) Date of Patent: *Nov. 20, 2007

(54) CHEST BRACE TO PREVENT COLLAPSE OF CHEST WALL

(76) Inventors: Charles Palmer, 660 Appenzell Dr., Hummelstown, PA (US) 17036; Jerome Matula, Jr., 224 Elliott Rd., Monroeville, PA (US) 15146-1932; Lance Busch, 34B Murrysville Rd., Trafford, PA (US) 15085; Eugene N. Scarberry, 208 Terrace Court Rd., Trafford, PA (US) 15085

( * ) Notice: Subject to any disclaimer, the term of this patent is extended or adjusted under 35 U.S.C. 154(b) by 0 days.

This patent is subject to a terminal disclaimer.

(21) Appl. No.: 11/128,765

(22) Filed: May 13, 2005

(65) Prior Publication Data

US 2005/0209543 A1 Sep. 22, 2005

Related U.S. Application Data

(63) Continuation of application No. 10/342,482, filed on Jan. 16, 2003, now Pat. No. 6,951,546, which is a continuation of application No. 09/528,878, filed on Mar. 20, 2000, now Pat. No. 6,533,739, which is a continuation-in-part of application No. 09/046,726, filed on Mar. 24, 1998, now Pat. No. 6,059,742, which is a continuation-in-part of application No. 08/560,267, filed on Nov. 21, 1995, now Pat. No. 5,820,572.

(51) Int. Cl.
*A61H 31/00* (2006.01)

(52) U.S. Cl. .................................. 601/41; 601/DIG. 6

(58) Field of Classification Search ............ 601/41–44; 128/202.12; 602/19, 20
See application file for complete search history.

(56) References Cited

U.S. PATENT DOCUMENTS

| | | | | |
|---|---|---|---|---|
| 3,489,140 A | * | 1/1970 | Mullikin | 601/97 |
| 5,327,887 A | * | 7/1994 | Nowakowski | 128/204.21 |
| 5,454,779 A | * | 10/1995 | Lurie et al. | 601/43 |

* cited by examiner

*Primary Examiner*—Danton DeMille
(74) *Attorney, Agent, or Firm*—Ohlandt, Greeley, Ruggiero & Perle L.L.P.

(57) ABSTRACT

A chest brace and method of using same that prevents the chest wall from buckling inwards during patient breathing by providing a distending force on the patient's thorax. The chest brace also restores the normal anterior-to-posterior chest dimensions by providing a distending force in this direction. The chest brace includes an anterior member adapted to overly a patient's chest. An adhesive mechanism secures the anterior member to a surface of such a patient. A support structure is coupled to the anterior member such that, in use, the support structure imparts a force on the anterior member in a manner so as to distend a thorax of such a patient.

6 Claims, 17 Drawing Sheets

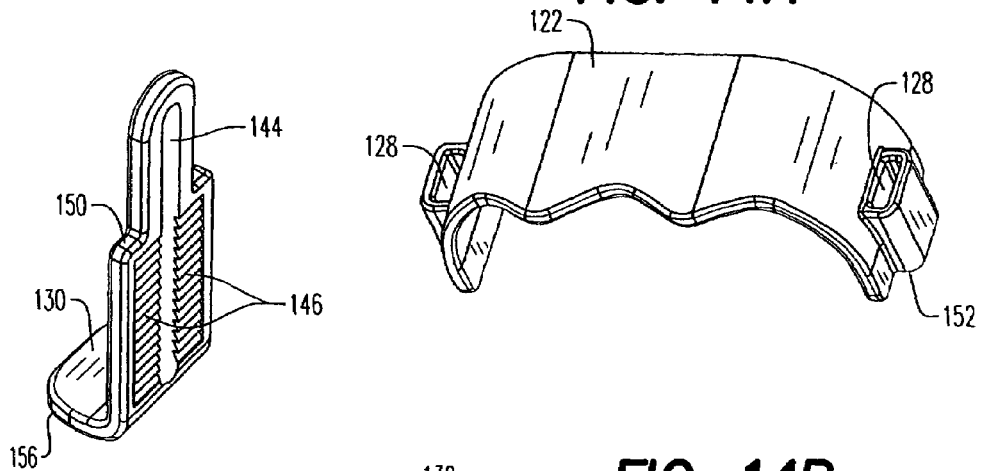
FIG. 14A
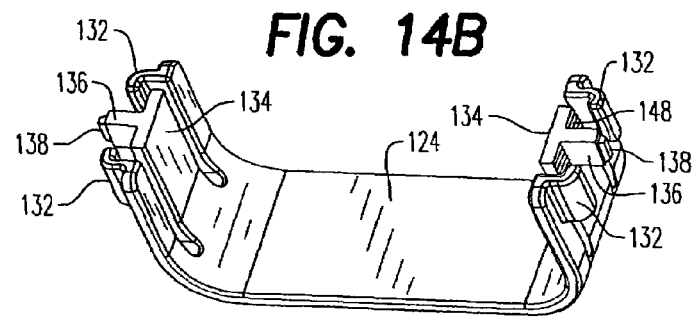
FIG. 14B
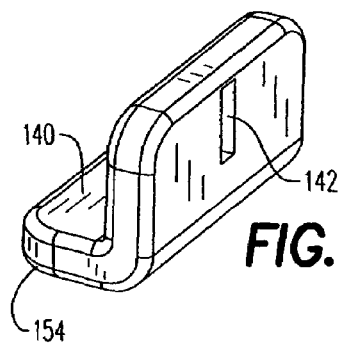
FIG. 14C
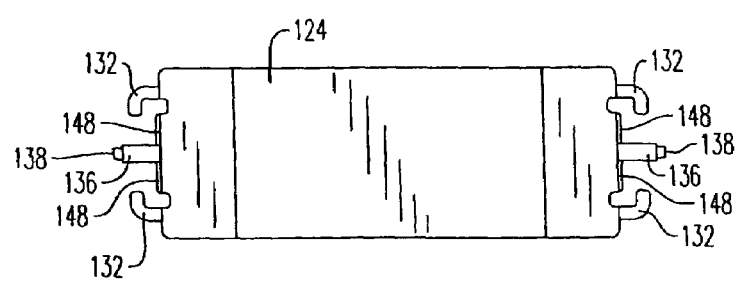
FIG. 14D
FIG. 14E

CHEST BRACE TO PREVENT COLLAPSE OF CHEST WALL

CROSS REFERENCE TO RELATED APPLICATIONS

This application is a Continuation of U.S. patent application Ser. No. 10/342,482. Filed Jan. 16, 2003, now U.S. Pat. No. 6,951,546, which is a Continuation of U.S. patent application Ser. No. 09/528,878, filed Mar. 20, 2000, now U.S. Pat. No. 6,533,739, which is a Continuation-in-Part of U.S. patent application Ser. No. 09/046,726, filed Mar. 24, 1998, now U.S. Pat. No. 6,059,742, which is a Continuation-in-Part of U.S. patent application Ser. No. 08/560,267, filed Nov. 21, 1995, now U.S. Pat. No. 5,820,572.

BACKGROUND OF THE INVENTION

1. Field of the Invention

The present invention relates to a chest brace and method of using a chest brace to prevent collapse of a chest wall of a patient, such as a neonate, to keep the lungs inflated. More particularly, the present invention pertains to an inexpensive chest brace that interacts with the skin covering the chest, rather than through applied negative air pressure, to provide a distending force on the chest wall to prevent its collapse, especially during respiration.

2. Description of the Related Art

Pulmonary insufficiency associated with immaturity is one of the most common life-threatening hurdles that confronts the premature newborn baby. The newborn's rib cage is soft and buckles easily during spontaneous respiration, particularly during inspiration. Underdevelopment of the intercostal muscles, lungs, or both contributes to the chest's deformability. In premature infants below 30 weeks gestation, thoracic wall elastic recoil is almost non-existent, so that the resting volume of the lungs is very close to or below their collapsed volume. Also, the relatively compliant chest wall tends to collapse as the diaphragm descends, resulting in a diminished tidal volume. As a result, most premature infants require assisted ventilation or a continuous distending pressure (CDP).

Continuous positive airway pressure (CPAP) is widely established as an effective method for preventing lung wall collapse, chest wall distortion, and for increasing oxygenation. Currently, CPAP is used almost exclusively in preference to continuous negative distending pressure. CPAP, however, is potentially hazardous to newborn infants with weakened respiratory systems. It is usually administered by nasal prongs, but has major limitations and serious side effects. These include: nasal trauma, difficulty in obtaining a good fit in very small infants, and high gas flows that cause airway cooling, drying, and obstruction of the nasal passages. During periods of crying and mouth opening, especially with high CPAP flows, there is a loss of pressure and the infant inhales room air. Frequent dislodgement of the nasal prongs makes nursing difficult, especially when associated with repeated bouts of desaturation. High or fluctuating saturation may increase the risk of retinopathy. Perhaps more serious are the circulatory disturbances, decreased venous return to the heart, diminished cardiac output, and increased intracranial hemorrhage.

Negative pressure applied intermittently around the chest has been used for more than a 100 years as a way of assisting ventilation in patients with respiratory failure. The iron lung is perhaps one of the best recognized negative pressure ventilators. Continuous negative distending pressure (CNP) is used to manage a number of specific conditions that produce respiratory failure in neonates and older infants. Negative distending pressure is highly effective and does not have many of the side effects of CPAP. Among its benefits with patients with respiratory disease syndrome are an increase in resting volume of the lung and arterial oxygen tension. There is also no need for an airway or nasal prongs. As opposed to positive distending pressure, CNP produces a decrease in intrathoracic and right arterial pressures, favoring venous return to the heart from parts of the body that are not exposed to the negative pressure. CNP further increases lung lymph flow and lung albumen transport. CNP also avoids the increases in pulmonary vascular resistance and pulmonary artery pressure that are observed with positive airway pressure. Recently, CNP has been re-introduced to treat infants with various pathological conditions.

While improvements have been made in the design of devices for generating extra-thoracic negative pressure, the devices are still difficult to attach to small newborns. Current designs consist of a cuirass or chamber and use vacuum around the chest or lower body to generate negative pressure. These devices require some form of electrical power supply, are relatively expensive, and are cumbersome. Technical difficulties are associated with temperature control, neck seals obstructing venous return, leaks around the seals and limited patient access. These devices also require considerable training and experience to operate and the technical problems make nursing difficult and frustrating. This limits the use of a potentially life saving treatment modality.

There are also situations where the thoracic shape of the newborn is not within normal thresholds, regardless of whether or not the chest is collapsing during respiration. A normal, healthy infant has a thoracic index between approximately 85%-95%. Thoracic index is defined as the ratio of the height of the chest, i.e., in an anterior-to-posterior direction or vice versa, over the width of the chest, i.e., in a lateral or side-to-side direction, when measured in the prone or supine position. Newborns with a thoracic index of less than 65%, for example, are generally not considered healthy. This decrease may or may not be related to collapsing of the chest during respiration. For example, a decreased thoracic index can be due to a malformation, or it may be present simply because the infant's chest has collapsed to a point at beyond which it can collapse no further. In such infants, there is a need to restore the thoracic index to its normal range. However, conventional assisted ventilation and CNP devices, which used primarily to prevent lung collapse, does little or nothing to improve the infant's thoracic index.

SUMMARY OF THE INVENTION

Accordingly, it is an object of this invention to provide a chest brace that overcomes the shortcomings of conventional techniques for preventing collapse of a patient's chest during spontaneous inspiration.

It is another object of this invention to provide a chest brace that provides a continuous distending pressure on the patient's chest so as to correct any collapse that is evident between breaths, i.e., at the end of expiration.

It is still another object of this invention, to provide a chest brace that provides continuous distending pressure on the patient's chest cavity without requiring vacuum seals.

It is yet another object of this invention to provide a chest brace that is particularly adapted for use with premature newborn babies.

It is still another object of this invention to provide a chest brace that is simple to attach, inexpensive, and does not require electrical power to operate.

It is a further object of the present invention to provide a chest brace and method of using such a brace to improve a patient's thoracic index even in the absence of chest collapse associated with respiration.

It is still a further object of this invention to provide a chest brace that is adapted to provide intermittent negative pressure ventilation for a patient without a need for endotracheal intubation.

These objects, among others, are achieved, according to one embodiment of the present invention, by providing a chest brace that includes an anterior member adapted to overly a patient's chest. An adhesive mechanism secures the anterior member to the surface of the patient. A support structure is coupled to the anterior member such that, in use, the support structure imparts a force on the anterior member in a manner so as to distend a thorax of the patient. In one embodiment of the present invention, the support structure includes a posterior member that is coupled to the anterior member using a mechanical linkage, so that the anterior member can be moved relative to the posterior member in a ratchet-like fashion, thereby imparting the distending pressure. This allows the patient to receive the distending force regardless of whether they are in the supine or prone position. In another embodiment of the present invention, the support structure includes a support structure, such as a shield, having a portion that is placed over the patient. The anterior member is suspended from the shield in a manner so as to impart the distending force on the patient's chest. The present invention also contemplates adhering a chest plate to the patient so that the anterior member can be selectively attached to the patient merely by securing it to the chest plate, thereby avoiding the need to remove the adhesive from the patient each time the patient is removed from the chest plate.

It is a further object of the present invention to provide a method of imparting a distending force on a thorax of a patient that that overcomes the shortcomings of conventional methods for preventing collapse of a patient's chest, improving the patient's thoracic index, or both. This object is achieved by providing a method that includes adhesively securing an anterior member of a chest brace structure to a patient's chest and imparting a force on the anterior member so as to distend a thorax of such a patient. Numerous techniques for imparting a force on the anterior member are discussed in detail below.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 14A-14D are perspective views of the components of the chest brace shown in FIG. 13, and FIG. 14E is a bottom view of the component shown in FIG. 14B;

DETAILED DESCRIPTION OF THE PRESENTLY PREFERRED EXEMPLARY MBODIMENTS OF THE INVENTION

Figure 1:
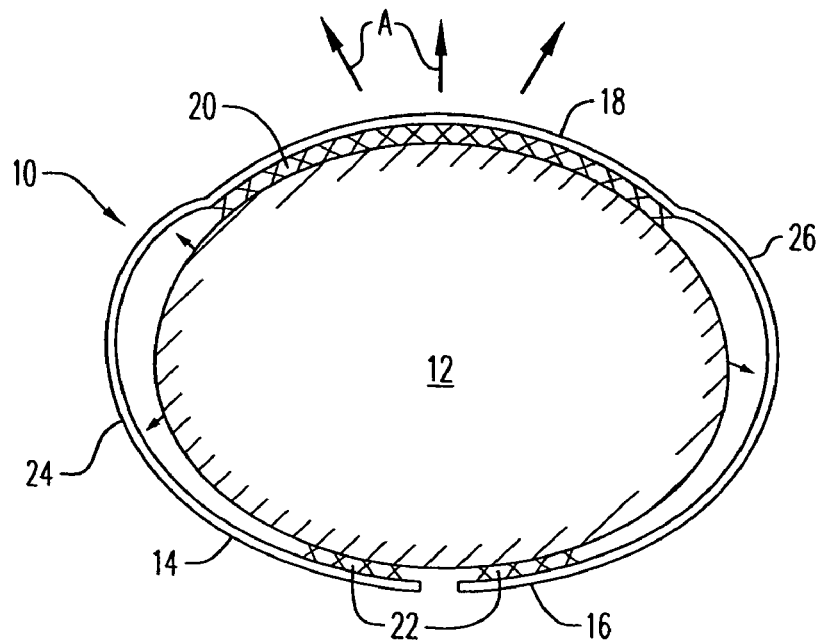
FIG. 1 is a schematic cross-section of a patient's chest showing a first embodiment of a chest brace according to the principles of the present invention.

A chest brace 10 according to the principles of the present invention is shown schematically in FIG. 1 and comprises a resilient metal core that is bent to surround a patient's chest 12, which is shown in cross-section. Chest brace 10 includes a pair of arms 14 and 16 bent around chest 12. A frontal resilient segment 18 adheres to the patient's chest wall by an adhesive structure 20 whose details are described below. In similar fashion, arms 14 and 16 adhere to the patient's back via an adhesive structure 22. The lateral segments 24 and 26 of chest brace 10 do not adhere to the patient's chest wall, thereby enabling lateral expansion and contraction during breathing.

Chest brace 10, when in the position shown in FIG. 1, exerts an outward distending force, as generally indicated by arrows A, via an adhesive structure 20 on the skin of the patient's chest. The distending force is accomplished by assuring that the resilient metal core assumes an approximately oval shape when arms 14 and 16 are bent around the patient, the oval shape being such as to cause a separation of frontal resilient segment 18 from the patient's chest wall. After the arms 14 and 16 have been adhered to the patient's back, a pressure is applied to frontal resilient segment 18, causing it to adhere to the patient's chest wall. The resiliency and inherent recoil of the compressed metal core causes an outward flexure of frontal resilient segment 18, and a continuous distending force A upon the patient's chest wall.

Figure 2:
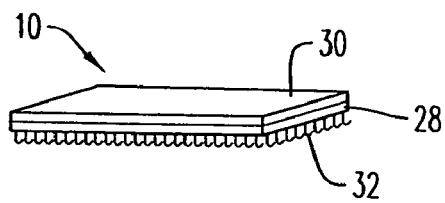
FIG. 2 shows a section of the chest brace of FIG. 1 illustrating its respective components.

Referring to FIG. 2, a small section of chest brace 10 is shown and illustrates that resilient metal core 28 is sandwiched between a soft material layer 30 and a Velcro™ layer 32. Velcro layer 32 only extends over the length of chest brace 10 that makes contact with a mating layer of Velcro that has been adhered, by an intermediate adhesive layer, to the patient's chest wall.

Figure 3:
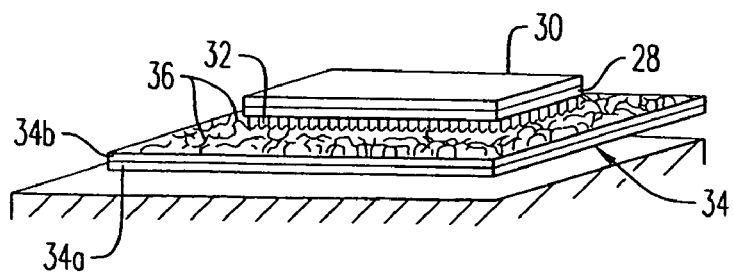
FIG. 3 illustrates a section of the chest brace of FIG. 1 adhered to a protective-adhesive strip that is bonded to a patient's chest.
Figure 4:
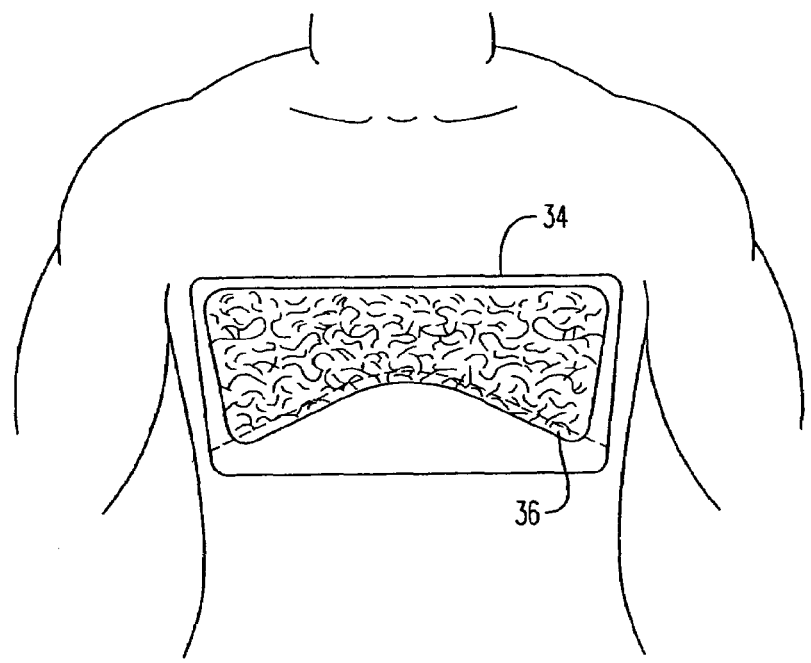
FIG. 4 is an anterior chest view of a patient showing the site of application of the protective-adhesive strip.

The Velcro/adhesive layer is shown in further detail in FIG. 3 and is comprised of a thin, elastic, transparent and self-adhesive hydrocolloid layer 34. Such materials are often used as a sterile skin dressing in neonatal intensive care units to protect newborn skin. Such materials consist of liquid absorbing particles in an elastic, self-adhesive mass 34a, covered on one side by a semi-permeable elastic and non-adherent polyurethane film 34b. The principal ingredients of such a hydrocolloid dressing are sodium carboxymethyl cellulose, synthetic block co-polymer, artificial tackifier and a plasticizer. Such a hydrocolloid material is manufactured by Coloplast, Inc., Tampa, Fla., and is marketed under the trademark COMFEEL™.

Adhered to film surface 34b of hydrocolloid layer 34 is a further layer of Velcro 36. Velcro layer 36 may be of the loop variety and Velcro layer 32 of the hook variety (or vice-versa) to enable a joinder therebetween. While the attachment mechanism is most preferably accomplished by the described, interacting Velcro layers, those skilled in the art will realize that any instrumentality which enables an adhesion between the patient's chest wall and the inner surface of chest brace 10 is within the scope of the invention.

Resilient metal core 28 is preferably comprised of strips of thin steel, e.g. 0.007-0.020 shim steel. The metal strips (or strip) are encased on their outer side with a soft material, such as moleskin™, available from the Johnson & Johnson Company, New Brunswick, N.J., and on their inner surface with Velcro layer 32. The thickness of each metal core 28 can be changed to suit the needs and dimensions of the patient. For example, an infant weighing 1,500 grams may need a chest brace 10 made of two steel strips, with each steel strip being approximately ¼ inch wide, thereby making the brace a little more than ½ inch wide.

FIGS. 4-7 illustrate the method of application of chest brace 10 to a patient. A strip of self-adhesive loop Velcro 36 is centered on the top of hydrocolloid layer 34 on the patient's anterior chest wall. Velcro 36 extends between the positions of the chest which tend to buckle inwards and a similar Velcro strip 40 is placed over hydrocolloid layer 42 posteriorly between the patient's scapulas. See FIG. 6.

Figure 5:
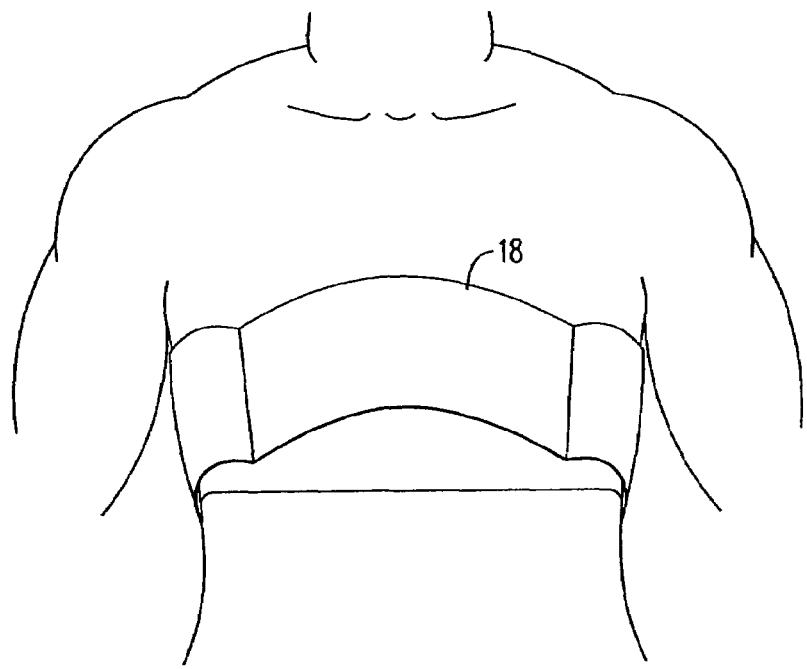
FIG. 5 is an anterior view of a patient showing the placement of the chest brace over the patient's chest.
Figure 6:
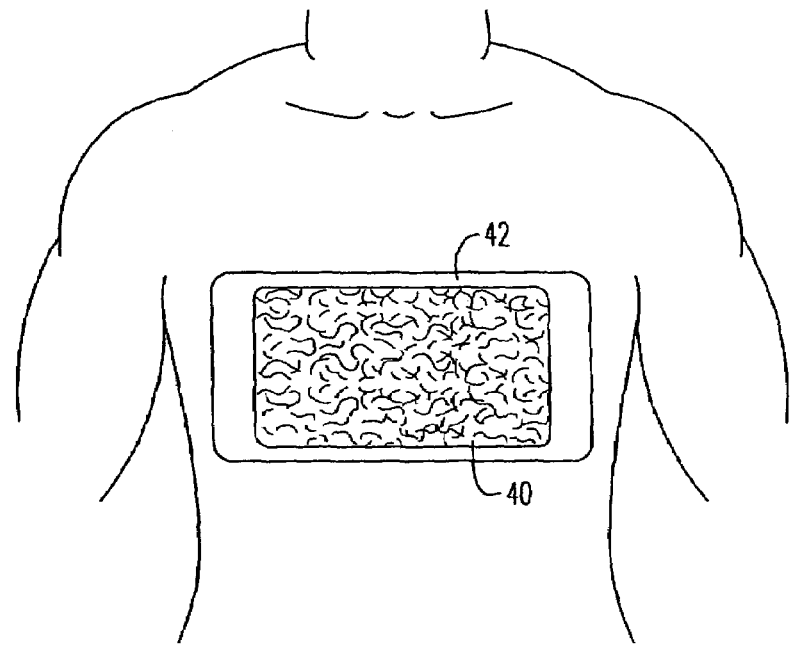
FIG. 6 is a posterior view of the patient showing placement of an adhesive strip over the patient's back.
Figure 7:
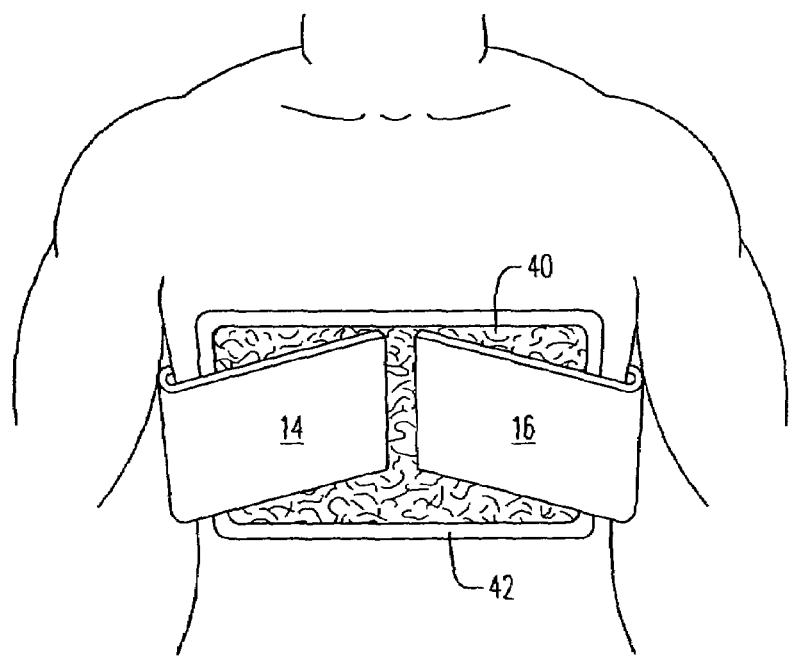
FIG. 7 is a posterior view of the patient showing two sides of the chest brace of FIG. 1 adhering to the adhesive strip of FIG. 6.

With the patient in the supine position, arm 16 of chest brace 10 is first brought into contact with Velcro layer 40 and is joined thereto by the corresponding Velcro layer on arm 16. See FIG. 7. Chest brace 10 is then swung anteriorly so as to encircle the patient's chest, arching over the xiphisternum and leaving at least ½ inch space between Velcro layer 36 on the patient's chest (see FIG. 4) and Velcro layer 32 on the underside of the resilient segment (see. FIG. 5). The free end of the chest brace 10, e.g., arm 18, is then attached onto Velcro layer 40, that is adhered to the patient's back by hydrocolloid layer 42.

Frontal resilient segment 18, positioned above the patient's sternum, is then indented by finger pressure so that the complementary Velcro layers lock together. It is preferred to have resilient segment 18 adhere to as much of anterior chest Velcro 36 as possible to disperse the load on the skin and the subcutaneous tissue. Once indented, the inherent recoil in the steel core exerts an outward pull on the chest wall. Sides 24 and 26 of the chest brace 10 are not attached to the patient and act as levers which pull out the chest anteriorly.

Figure 8:
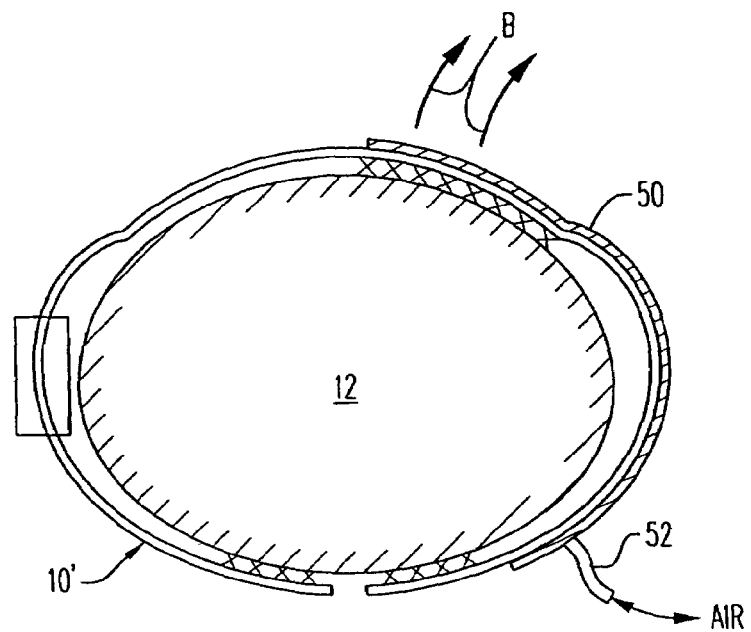
FIG. 8 is a cross-section of the patient with a second embodiment of a chest brace, which includes a pneumatic tube for providing active negative pressure ventilation to the patient.

In addition to providing rigidity for the patient's chest wall and a continuous negative distending pressure, a second embodiment of a chest brace 10' is adapted to provide active ventilation. Referring to FIG. 8, the exterior surface of chest brace 10' includes an air bladder 50 that is bonded thereto. By controlling the amount of air within air bladder 50, via tube 52, the stiffness of bladder 50 can be altered to control the amount of outward pull of chest brace 10', as indicated by arrows B. More specifically, filling bladder 50 with air changes its shape, and as bladder 50 straightens, it pulls the brace away from the chest. When pressure is released from air bladder 50, chest brace 10' is enabled to resume its original position by the natural resiliency of its metal core. In such manner, ventilation of the patient can be assisted by periodically altering the air pressure within air bladder 50.

Figure 9:
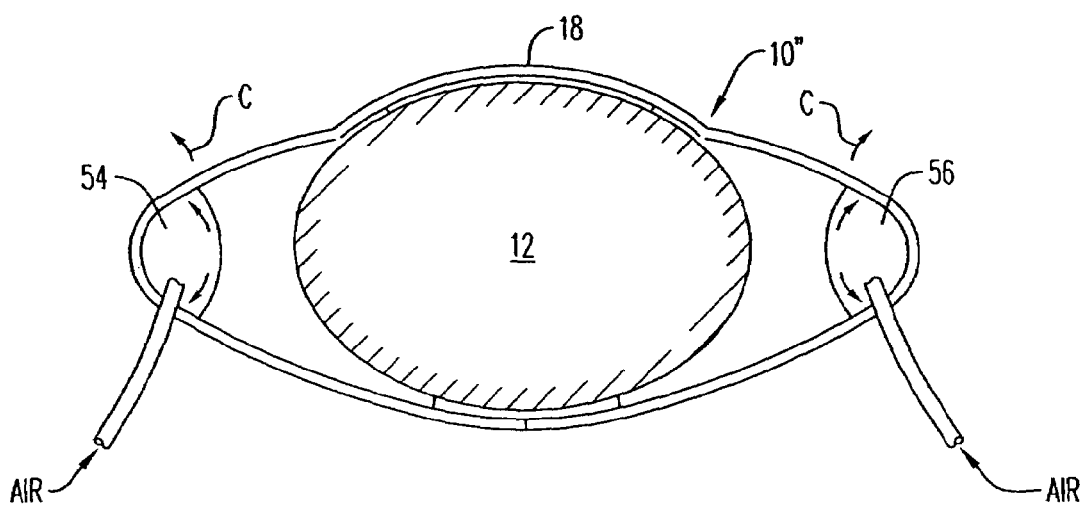
FIG. 9 is a cross-section of the patient with a third embodiment of a chest brace, which includes interior distendable balloons for providing controllable negative pressure ventilation to the patient.

In FIG. 9, a third embodiment of a chest brace 10" is shown. Chest brace 10" provides the same ventilation function as chest brace 10' of FIG. 8 except that in this case, a pair of bladders 54 and 56 are positioned within a chest brace 10". Inflation and deflation of the bladders, either individually or simultaneously, controls the position of frontal resilient segment 18 of chest brace 10", as generally indicated by arrows C. In such a manner, ventilation of the patient is assisted.

Figure 10:
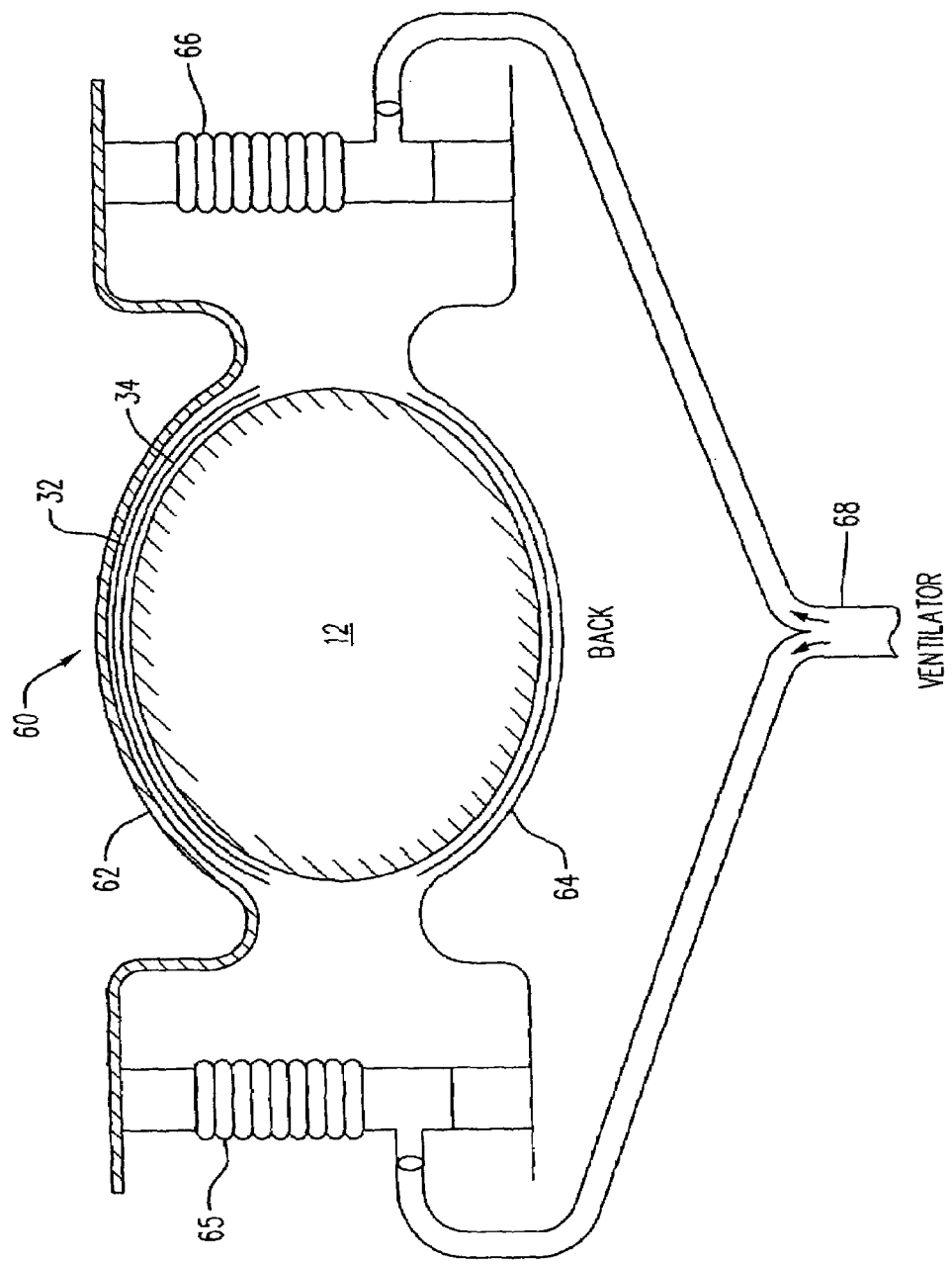
FIG. 10 is a cross-section of a patient with a fourth embodiment of the chest brace, which includes corrugated tubing for imparting controllable negative pressure ventilation to the patient.

FIG. 10 illustrates a fourth embodiment of a chest brace 60 that comprises a pair of separated brace members 62 and 64. Anterior brace member 62 is adhered to the patient's chest wall via the same connection mechanism as described above. Similarly, posterior brace member 64 is adhered to the back of the patient in the manner described above. The spacing between brace members 62 and 64 is controlled by air pressure within a pair of corrugated respirator tubes 65 and 66. Thus, as pressure is increased within corrugated tubes 65 and 66, anterior brace member 62 moves away from posterior brace member 64. Through the action of the Velcro interconnection between anterior brace member 62 and the patient's chest wall, the patient's chest wall moves outwardly. When, however, pressure is reduced within corrugated tubing 65 and 66, a vacuum is created thereby causing a squeezing action on the patient's chest between brace numbers 62 and 64. In such manner, the patient's respiration is assisted. Control of air pressure in tubes 64 and 66 is via an input 68 from a ventilator system which provides the necessary alterations in air pressure.

While FIGS. 8-10 illustrate air as the medium used to control the actuation of the chest brace, it is to be understood that other fluids, such as an inert gas or water, can be used to hydraulically or pneumatically actuate these chest brace devices. Furthermore, rather than using these chest braces to provide or assist active ventilation, they can also be used to provided a continuous distending force of the chest wall to prevent its collapse, with the amount of fluid delivered to the actuating bladder or tubes controlling the magnitude of the distending force. Using the chest brace of FIGS. 8-10 in this manner has the benefit in that the amount of distending force applied to the patient's chest wall can be easily controlled and altered and the brace need not be flexed in order to adhere it to the patient. Instead, each piece can be applied to the patient, and, when properly fitted, the bladder or tube can be actuated to apply the desired degree of distending force to the patient.

Figure 11:
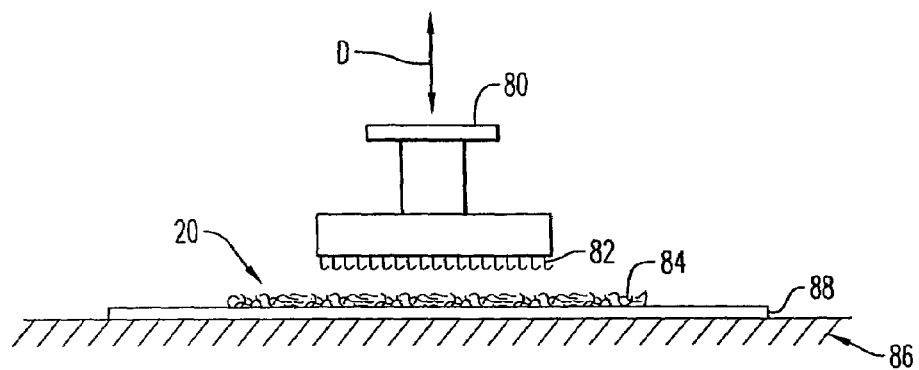
FIG. 11 is a side view of a T-piece that is usable with the protective-adhesive layer to enable manual compression and distension of the chest wall.

The presence of adhesive structure 20 on a patient's chest renders it further possible to manually compress and distend the chest. In FIG. 11, a T-shaped plunger 80 includes a distal layer 82 of Velcro, which attaches to Velcro layer 84 that is, in turn, adhered to chest wall 86 by adhesive layer 88. Manual manipulation of plunger 80 allows compression and distension of chest wall 86, as indicated by arrow D. This produces compression and emptying of the heart, while distension produces a filling of the heart and lungs.

Figure 12:
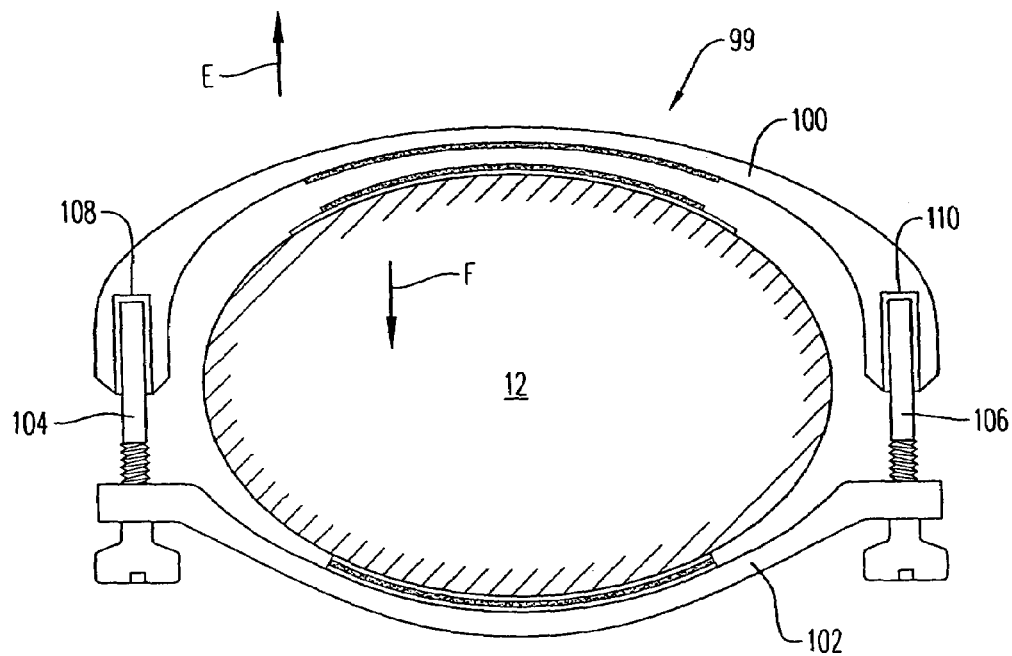
FIG. 12 is a cross-section of a patient with a fifth embodiment of the chest brace, which includes adjustable screws for imparting controllable distension to a patient's chest.
Figure 13:
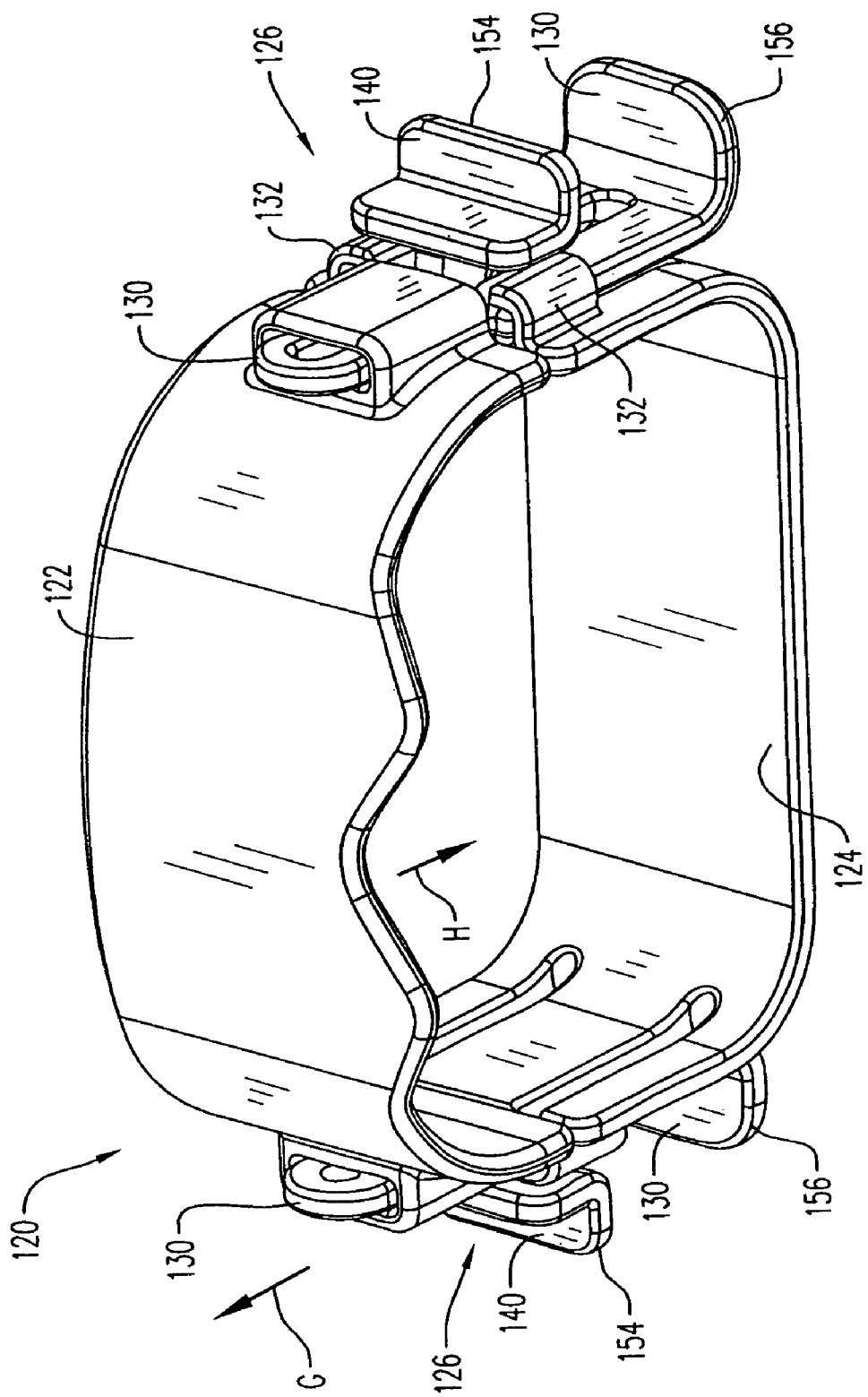
FIG. 13 is a perspective view of a sixth embodiment of a chest brace according to the principles of the present invention.
Figure 15:
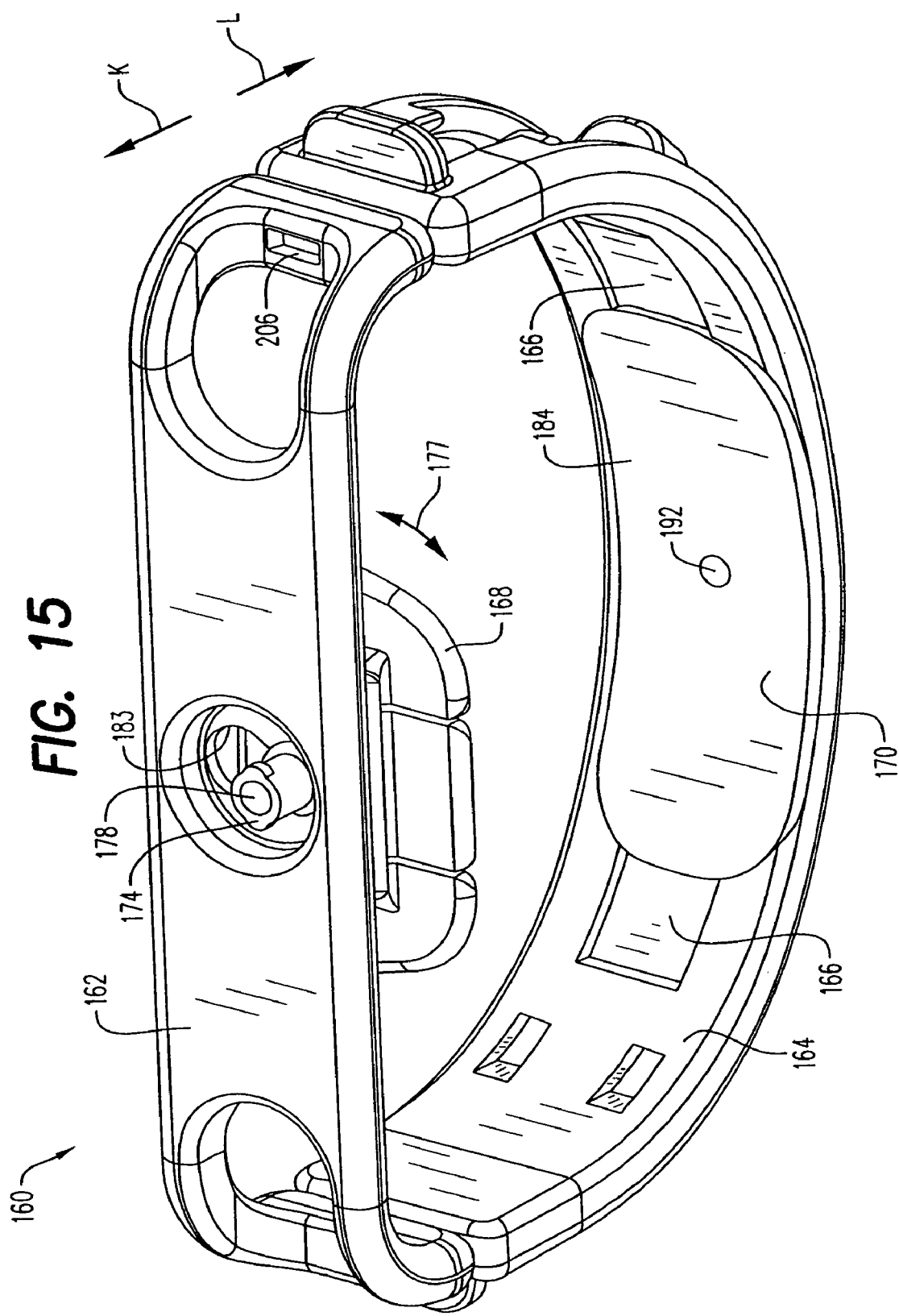
FIGS. 15, 16, and 17 are top, bottom, and exploded perspective views, respectively.
Figure 16:
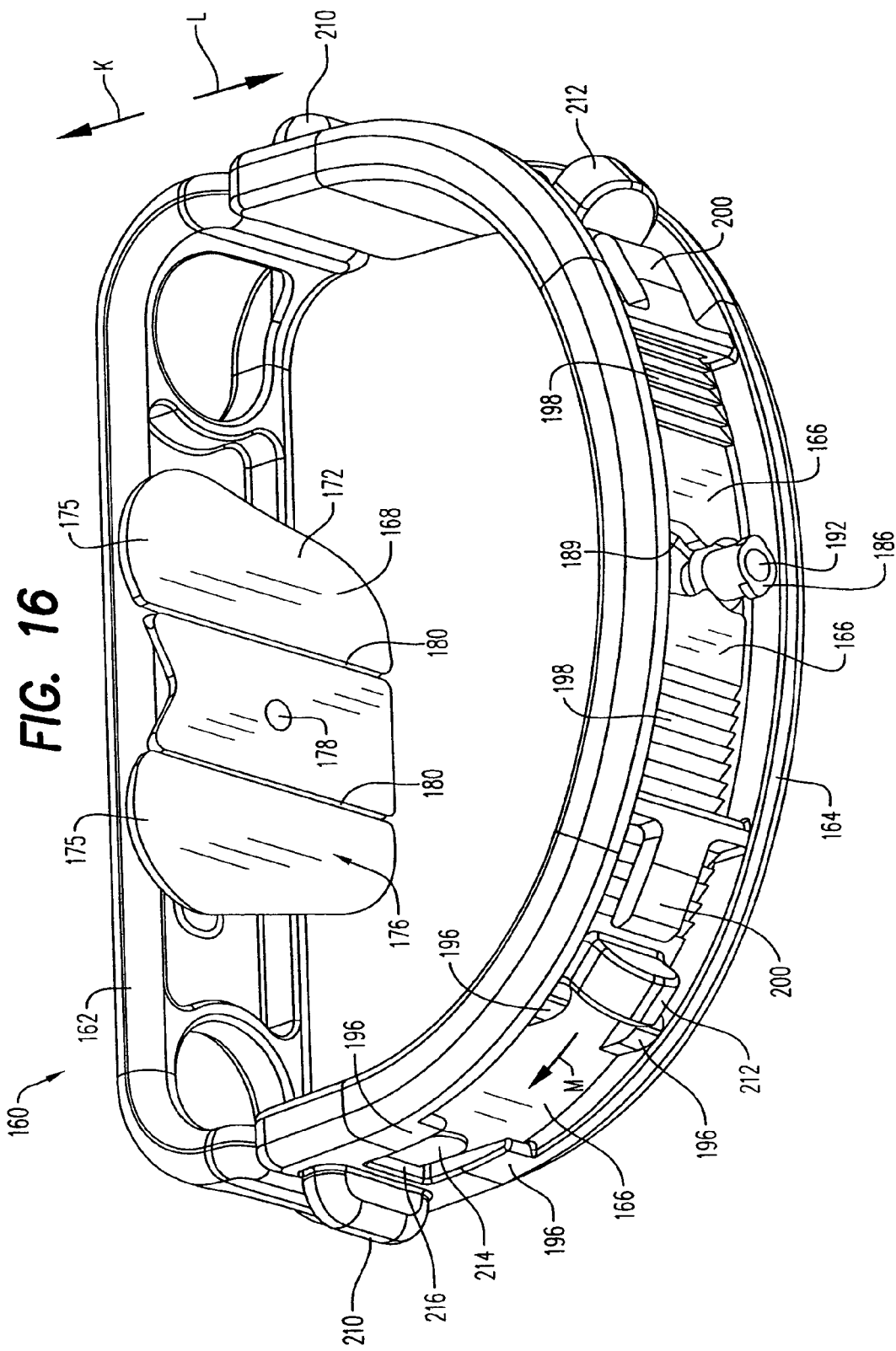
Figure 17:
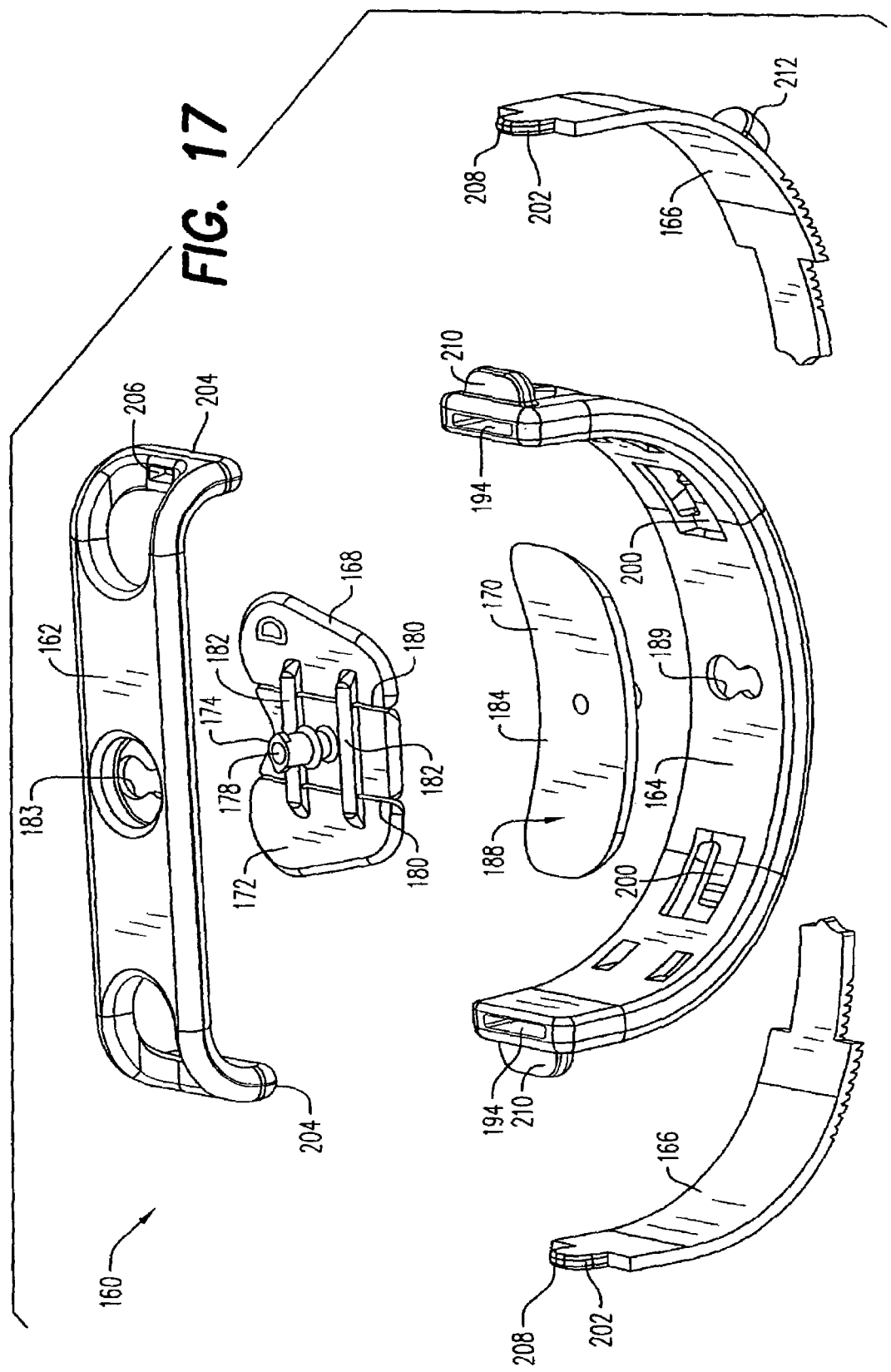
Figure 18:
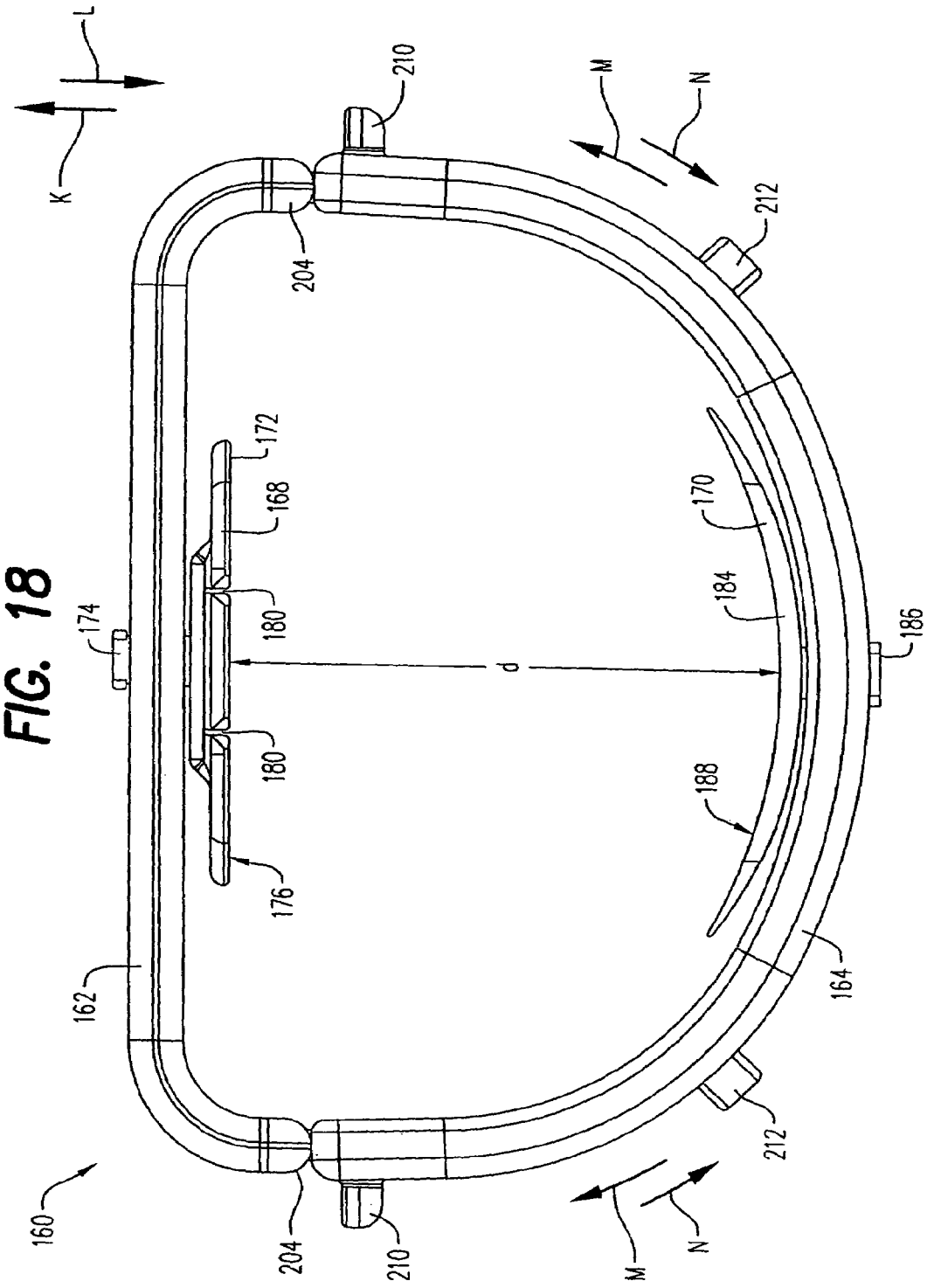
FIG. 18 is a side view of seventh embodiment of a chest brace according to the principles of the present invention.
Figure 19A:
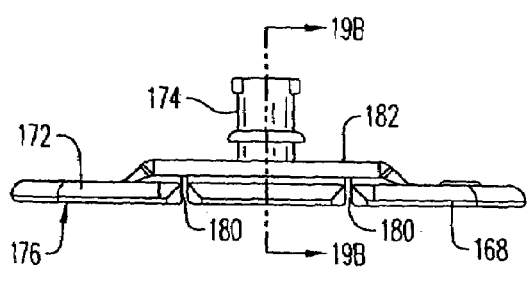
FIG. 19A is a side view of a chest plate used in the chest brace of FIGS. 15-18.
Figure 19B:
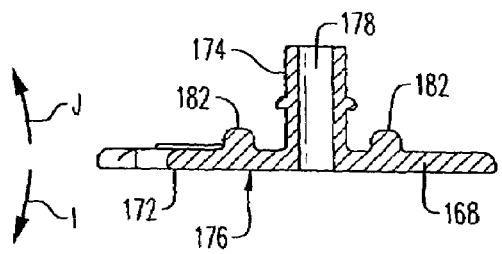
FIG. 19B is a cross-sectional view of the chest plate taken along line 19B-19B of FIG. 19A.
Figure 20A:
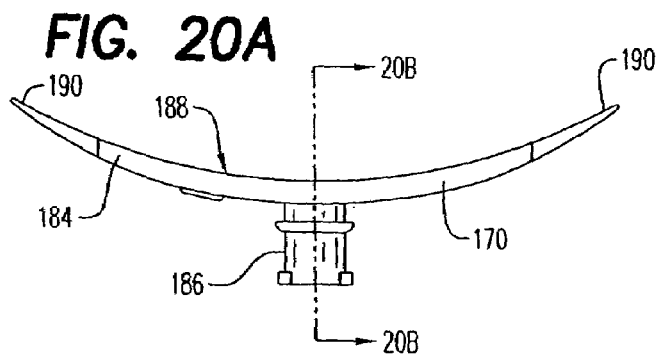
FIG. 20A is a side view of a back plate used in the chest brace of FIGS. 15-18.
Figure 20B:
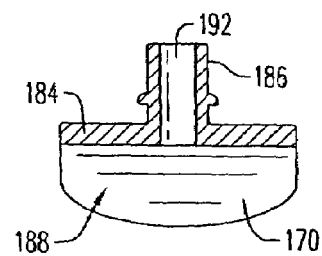
FIG. 20B is a cross-sectional view of the back plate taken along line 20B-20B of FIG. 20A.
Figure 21:
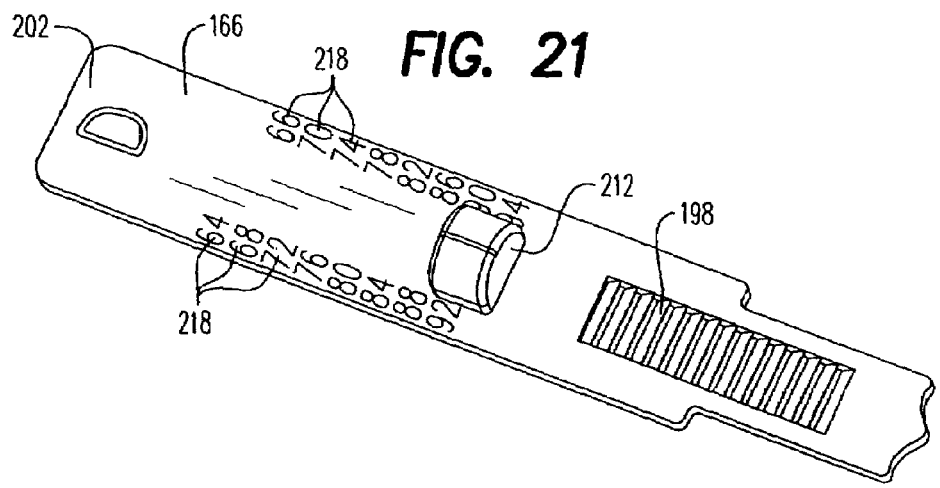
FIG. 21 is a perspective view a flexible linkage used in the chest brace of FIGS. 15-18.

In FIG. 12, a fifth embodiment of a chest brace 99 is shown, which comprises a pair of separated brace members 100 and 102. Anterior brace member 100 is adhered to the patient's chest wall via the same adhesive connection mechanism described above. Similarly, posterior brace member 102 is adhered to the back of the patient in the manner described above. The spacing between brace members 100 and 102 is controlled by a pair of screws 104 and 106, each of which is threaded into posterior brace member 102. The distal end of each of screws 104 and 106 is positioned in a respective orifice 108, 110 in brace member 100. The diameters of orifices 108 and 110 are sufficiently large as to receive, without interference, the distal ends of screws 104 and 106 so that the screws are free to move within the orifice.

Adjustment of screws 104 and 106 to move anterior brace member 100 away from posterior brace member 102, as indicated by arrow E, distends a patient's chest. In use, the weight of the patient adhered to anterior brace member 100 urges anterior brace member 100 toward posterior brace member 102, as indicated by arrow F, so that the anterior and posterior brace members remain in an engaged relation. Further, if the patient is being actively ventilated or breaths spontaneously, the clearances between orifices 108 and 110 and the distal ends of screws 104 and 106 enable brace member 100 to rise when air enters the patient's lungs, assuming, or course, that anterior brace member 100 and posterior brace member 102 are positioned close enough to one another that the movement of the patient during respiration moves anterior brace member 100 away from posterior brace member 102. During the exhalation cycle, brace member 100 falls until the distal ends of screws 104 and 106 hit the bottoms of orifices 108 and 110, respectively. This action allows for free movement of the patient's chest during inhalation while preventing collapse of the patient's chest wall during exhalation due to the interaction of brace member 100 and the adhesive layer that is adherent to the patient's chest.

It should be understood that the foregoing description is only illustrative of the invention. Various alternatives and modifications can be devised by those skilled in the art without departing from the invention. For instance, while screws 104 and 106 are shown as threaded into brace member 102, they could be threaded into brace member 100 and orifices 108 and 110 could be positioned in brace member 100.

FIGS. 13 and 14A-14E illustrate a sixth embodiment of a chest brace 120 and its components according to the principles of the present invention. Chest brace 120 includes an anterior member 122 that overlies the patient's chest and a posterior member 124 that overlies the patient's back so that the patient is positioned in the center of the ring defined by the anterior and posterior members. Although not shown, anterior member 122 and posterior member 124 are attached to the chest and back of the patient, respectively, using the same adhesive connection mechanism described above with respect to FIGS. 1-12. A pair of mechanical linkages 126 on each end of anterior member 122 and posterior member couple the anterior and posterior members to one another.

The general function of chest brace 120 is much the same as chest brace 99 in FIG. 12. Namely, mechanical linkages 126 include a ratchet mechanism that allows anterior member 122 to be moved away from posterior member 124 in the direction of arrow G to a desired position. The ratchet mechanism prevents any movement back toward the posterior member in the direction of arrow H, so that the anterior member is maintained at a fixed distance from the posterior member to apply a distending force on the patient's chest. Mechanical linkages 126 also allow anterior member 122 to move unimpeded farther away from posterior member 124 beyond the fixed distance, so that the patient's chest can expand freely during respiration. However, as noted above, chest brace 120 will not allow anterior 122 member to move any closer to posterior member 124 than the fixed distance set using the ratchet mechanism, thereby preventing the patient's chest from collapsing.

In the illustrated exemplary embodiment, anterior member 122 includes channels 128 at each end for receiving a sliding member 130 in mechanical linkage 126. Channel 128 and sliding member 130 are sized and configured to allow for free translation movement therebetween, i.e., so that anterior member 122 can slide up and down on sliding members 130 freely. Posterior member 124 includes a pair of protrusions 132 at each end for retaining sliding member 130 in an engaged relation, while also allowing translational movement of the sliding member relative to the posterior member. Posterior member 124 also includes a central post 134 at each end, with a protrusion 136 provided at the distal end of each post. An engaging tab 138 is provided at the end of protrusions 136. The cantilevered arrangement of posts 134 on posterior member 124 allows a small amount of lateral (side-to-side) movement of the distal end of the post.

Mechanical linkages 126 each include a retaining tab 140 that is fixed to protrusions 136 on central posts 134 by securing engaging tab 138 in a slot 142 provided in retaining tab. When assembled in this manner, protrusion 136 is disposed in a slot 144 in sliding member 130, with retaining tab 130 and protrusions 132 keeping sliding member 130 in an engaged relation with posterior member 124. Sliding members 130 include teeth 146 and central posts 134 include teeth 148, so that when assembled, teeth 146 engage teeth 148 in a ratchet fashion. More specifically, the teeth on sliding member 130 and posterior member 124 allow sliding member 130 to move incrementally upward, i.e., in direction G, as teeth 146 and 148 slip past one another, but prevent downward movement of the sliding member, i.e., in direction H, by engagement of teeth 146 and 148. The flexing of central posts 134 and the configuration of teeth 146 and/or 148 allows this ratchet movement of the sliding member relative to the posterior member.

Each sliding member 130 includes a shoulder 150 that engages an edge 152 of anterior member 122 for carrying the anterior member upward as the sliding members move upward. Once the fixed or operative position of the sliding member is set, further upward movement of anterior portion 122 lifts the anterior member off shoulders 150. In this manner, anterior member 122 can slide up and down on the distal ends of sliding members 130 but cannot drop below the fixed position because of the engagement between shoulders 150 of sliding members 130 and the ratchet mechanism.

Moving sliding members 130 and anterior member 122, upward, i.e., in direction G, is facilitated by a protruding portion 154 on retaining tabs 140 and a protruding portion 156 on sliding members 130. More specifically, to raise anterior member 122 off of posterior member 124, the user need only squeeze or pinch protrusions 154 and 156 together.

FIGS. 15-18 illustrate a seventh embodiment of a chest brace 160 according to the principles of the present invention, and FIGS. 19A-21 illustrate selected components of chest brace 160 in greater detail. Chest brace 160 includes an anterior member 162, a posterior member 164, and flexible linkages 166 that couple anterior member and posterior member 164. In the previous chest brace embodiments, the anterior and posterior members are directly coupled to the patient via an adhesive mechanism. In this embodiment, however, anterior member 162 is coupled to the patient via a chest plate 168, and posterior member 164 is coupled to the patient via a back plate 170. Chest plate 168 and back plate 170 are releaseably secured to anterior member 162 and posterior member 164, respectively, via an interlocking mechanism described in greater detail below. Chest plate 168 and back plate 170 can have any number of configurations and sizes, so long as the function of securing the patient's chest to the anterior member 162 and the patient's back to the posterior member 164, respectively, are accomplished.

This configuration for chest brace 160 minimizes the amount of material that is adhered to the patient, while still allowing the patient to be quickly and easily attached to the remainder of the chest brace as needed. As a result, a neonate, for example, can be easily and quickly disengaged from the major components of the chest brace for breast feeding, cleaning, diaper changing, examination, mother or father bonding, etc., and then returned to the chest brace structure without having to remove the adhesive applied to the infant. It can be appreciated that removing and reapplying the adhesives is a much more time consuming and cumbersome process that merely detaching chest plate 168 and back plate 170 from anterior member 162 and posterior member 164, respectively.

A further benefit of this embodiment for the chest brace is that the major components of chest brace 160, i.e., anterior member 162, posterior member 164, and flexible linkages 166, can be used on a relatively large number of patients, with only the chest plate and back plate being patient-specific. This minimizes the number of different chest brace components that are necessary and that must be kept on hand in order to accommodate a wide variety of patients.

Chest plate 168 and back plate 170 are preferably made from poyurethane. However, the present invention contemplates that other plastic or semi-plastic materials, such as vinyl, can be used for the chest plate and back plate. In addition, it is preferable that the chest plate and back plate be made from a transparent material to allow a caregiver, for example, to visually monitor the patient's tissues underlying each plate without having to remove these plates.

Chest plate 168 includes a relatively planar base 172 and a stem 174 attached thereto for securing the chest plate to anterior member 162. In the illustrated embodiment, base 172 includes a first end 173 having a generally linear edge and a second end opposite the first end having a pair of lobes 175. When properly positioned in the patient, first end 173 is closer to the patient's head than lobes 175 so that the chest brace overlies the patient's rib cage.

An exposed surface 176 of the base 172, which is opposite stem 174, provides a surface that adheres to the patient. In a preferred embodiment of the present invention, a hydrogel adhesive of the type used conventionally to secure EKG electrodes to a patient are used as an adhesive material to bond surface 176 of chest plate 168 to the surface of the patient. A hydrogel adhesive, such as the hydrogel adhesive identified as RG73P and manufactured by Ludlow Technical Products of Huntington Beach, Calif., which is a water-based adhesive, is preferred because, as a hydrogel, it dissolves or has reduced adhering capability when flushed with water. Therefore, the adhesive can easily removed from the patient with a minimal amount of tissue damage and pulling using only water as a solvent. Although a water-based hydrogel is believed to be preferably due to its biocompatibility with human tissue, the present invention also contemplates using other types of hydrogels, such as oil-based adhesives, to secure the back plate and chest plate to the surface of the patient.

To facilitate detachment of the chest plate from the patient, a channel 178 is defined in stem 174. Channel 178 allows a liquid solvent capable of dissolving the hydrogel to be inserted between surface 176 and the surface of the patient. The insertion of such a liquid between surface 176 and the surface of the patient also provides a pneumatic release mechanism tending to urge surface 176 and the surface of the patient apart.

Because it is important that planar base 172 adhere securely to the surface of the patient, which is not planar, but is oftentimes slightly caved-in, i.e., concave, the present invention contemplates providing channels 180 in a lengthwise direction of the base plate, i.e., in a direction generally aligned with the length of the patient on which the chest plate is placed. Channels 180 separate the base plate into several portions that have a small degree of movement relative to one another, as indicated by arrows I and J. See FIG. 19A. A pair of support members 182 are provided on surface of base 172 opposite surface 176 act as hinges to maintain the structure integrity of the base. Channels 180, together with the small degree of flexibility present in most plastics, such as polyurethane, used in support members 182 allow the planar base plate to be contoured, at least somewhat, to match the contour of the patient, and, in particular, to better match the concavity a patient whose chest is slightly caved-in.

Preferably, the degree of movement in direction J is greater than in direction I so that the base plate can conform to the patient's concave chest while not buckling when a load is applied to surface 176. Channels 180 provide this ability because they allow for a bending movement in direction J, but limit the amount of movement in direction I. Movement in direction I is limited because the channel walls impinge on one another after a predetermined amount of deflection in direction I, thereby preventing any additional deflection so that the base plate does not fold in on itself.

While the figures illustrate base 172 has having two channels defined therein, the present invention contemplates that no channels, one channel, or more than two channels can be provided. For example, internal structures (wires, tubes, or etc.), scoring, or materials having different bending properties can be used in base 172 to provide the desired degree of flexibility in virtually any direction of the base so that it can be contoured to match the surface of the patient. The depth, width, and shape of the channels can also be varied depending on the desired degree of flexibility for base 172. Also, the location of the channels and their shape in the base plate can be other than that shown in the figures.

Although support members 182 are shown as being integrally formed with base 172, the present invention contemplates that such support members can be added after the base is formed. They can also be defined within the base and need not have the specific size, shape, and configuration illustrated. The present invention also contemplates varying the stiffness of the material defining the base plate, providing internal reinforcing structures, varying the shape or thickness of the base itself to achieve the functions of channels 180, support members 182, or both.

In the illustrated exemplary embodiment, chest plate 168 attaches to anterior member 162 in a slot and key configuration by interlocking stem 174 in a channel 183 defined in the center of the anterior member. Channel 183 includes a first, relatively wide portion, having a diameter greater than that of stem 174 so that the stem can readily insert into the first portion of the channel. Channel 183 also includes a second, narrower portion, so that once the stem is moved into the second, narrower portion of the channel, the stem and, hence, the chest plate, are engaged to anterior member 162. A flaring may be provided on the stem to facilitate such attachment.

The present invention contemplates that second portion of channel 183 and stem 174 can be sized such that the stem is prevented from moving in the second portion of the channel once it is moved into this portion of this channel. This configuration causes chest plate 168 and anterior member 162 move as a single piece. An alternative embodiment of the present invention, however, contemplates allowing stem 174 to rotate, as generally indicated by arrow 177, within channel 183, as well as move in a vertical direction, as indicated by arrows K and L in FIG. 15. Flanges can be provided on stem 174 to limit the movement in direction L or K. If desired, protrusions or other such structures can be provided on stem 174 to limit the rotational movement.

It is to be understood, that the stem and channel interlocking technique described immediately above for securing the chest plate to the anterior member represents only one of a number of techniques for selectively engaging these components of the chest brace contemplated by the present invention. For example, the present invention contemplates using a snap-fit configuration, bolt and screw, tongue and groove, or hook and loop technique for selectively interlocking chest plate 168 and anterior member 162.

Back plate 170 includes a base plate 184 that is curved to match the general curvature of the back of the patient and a stem 186 attached thereto. A surface 188 of base 184 adheres to the back of the patient, preferably using the above-described hydrogel adhesive. In the illustrated embodiment, the thickness of the back plate is the greatest at its center and decreases as the distance from the center increases, so that distal ends 190 are relatively more flexible than the center portion. See FIG. 20A. This allows distal ends 190 to have greater flexibility for adhering to the surface of the patient farther form the centerline, wherein the curvature increases as the distance from the center of the back increases. Like stem 174 in chest plate 168, stem 186 of back plate 170 includes a channel 192 so that a liquid, preferably a solvent, can be inserted between surface 188 and the surface of the patient. As noted above, the insertion of such a liquid between surface 188 and the surface of the patient assists in dissolving or loosening the adhesive securing surface 188 to the patient and provides a pneumatic release mechanism tending to urge surface 188 and the surface of the patient apart.

In the illustrated exemplary embodiment, back plate 170 attaches to posterior member 164 by interlocking stem 186 in a channel 189 defined in the center of the posterior member. Channel 189, like channel 183 in anterior member 162, includes a first, relatively wide portion, having a diameter greater than that of stem 186 so that the stem can readily insert into the first portion of the channel. Channel 189 also includes a second, narrower portion, so that once the stem is moved into the second, narrower portion of the channel, the stem and, hence, the back plate, is engaged to posterior member 164. A flaring may be provided on the stem to facilitate such attachment.

It is to be understood, that the stem and channel interlocking technique described immediately above for securing the back plate to the posterior member represents only one of a number of techniques for selectively engaging these components of the chest brace contemplated by the present invention. For example, the present invention contemplates using a snap-fit configuration, bolt and screw, tongue and groove, or hook and loop technique for selectively interlocking back plate 170 and posterior member 164.

Anterior member 162, a posterior member 164, and flexible linkages 166 cooperate in a manner similar to that described above with respect to chest brace 120 of FIG. 13 in that the flexible linkage allows the anterior member to be moved away from the posterior member, as indicated by arrow K, in a ratchet fashion to apply a distending force on the patient's chest to prevent its collapse. Because a distending force is acting on both the front and back of the patient in the current embodiment of FIGS. 15-21, as is also the case with the devices shown in FIGS. 1, 8, 9, 10, 12, and 13-14E, the patient can be placed in the supine position or in the prone position without compromising the effectiveness of the distending properties of the chest brace. This is particularly important in situations where the patient will be wearing the chest brace of extended periods of time, where the position of the patient needs to be frequently changed.

Once anterior member 162 is moved to a set point, which is selectable by the user, the ratchet mechanism, which is provided by the interaction of flexible linkages 166 and posterior member 164, prevents the anterior member from moving back toward the posterior member, i.e., in the direction indicated by arrow L, thereby maintaining the distending force to splint the patient's chest from collapsing. However, once in the set position, additional movement of the anterior member in direction K away from the posterior member is possible because there is no structure preventing such movement. If the patient is wearing the chest brace and it is at its set point, further expansion of the patient's chest, which could occur if the patient inhales deeply or coughs or is on mechanical ventilation with a positive airway pressure sufficient to cause the chest to rise, for example, results in additional unimpeded outward movement of the anterior member relative to the posterior member, i.e., in direction K, to accommodate this additional chest distention.

Flexible linkages 166 are provided in channels 194 defined at least at the ends of in posterior member 164. Posterior member 164 includes various protrusions 196 that serve to maintain the flexible linkages in an engaged relation with the posterior member. Flexible linkages 166 are moveable within the channels defined in posterior member 164, as generally indicated by arrows M and N in FIG. 18. However, movement of the flexible linkages is controlled in a ratchet-like fashion. This is accomplished by providing a number of teeth 198 in each linkage and a cantilever level 200 on the posterior member associated with each flexible linkage. Cantilever level 200 has at least one ratchet tooth for engaging teeth 198 in a manner that permits incremental movement of flexible linkages 166 relative to posterior member 164 in direction M, but prevents movement in direction N when the teeth in cantilever level 200 engage teeth 198 in flexible member 166.

As flexible linkage 166 moves in direction M, an engaging end 202 engages ends 204 of anterior member 162. Preferably, ends 204 includes a slot 206 for receiving a protrusion 208 provided on engaging ends 202 of flexible linkages 166. The engagement between engaging end 202 of flexible linkage 166 and ends 204 of anterior member 162 is such that the anterior member can be freely removed or pulled off of the ends of the flexible linkage. It can be appreciated that the depth at which the engaging end of the flexible linkage is inserted into the stop in the end of the anterior member dictates the amount of movement that is available before the anterior member detaches from the ends of the flexible member.

Movement of flexible linkages 166 in direction M is facilitated by tab 210 provided on posterior member 164 and tab 212 provided on the flexible linkages. To move anterior member 162 away from posterior member 164 in direction K, the user need only squeeze or pinch tabs 210 and 212 together. The amount of travel of flexible member 166 in the channel of posterior member 164 is limited by tab 212 engaging a removable stop 214 on each end of the posterior member. The present invention contemplates that either or both of these stops can be broken off of the posterior member or bent up to allow additional advancement of the flexible member in direction M. In which case, a portion 216 of the frame of posterior member 162 would act as a stop for tab 212.

Flexible linkage 166 preferably includes a plurality of indicia 218 that represent the distance d between the center of the chest plate and the center of the back plate in the assembled chest brace. This allows the same chest brace to be repeatedly used without having to reestablish the correct settings for the displacement between the anterior member and the posterior member. Indicia 218 can be viewed, for example, through a window provided in the ends of posterior member 164 (not shown) or as they are exposed upon exiting channel 194 as flexible linkage 166 is moved in direction M.

Figure 22:
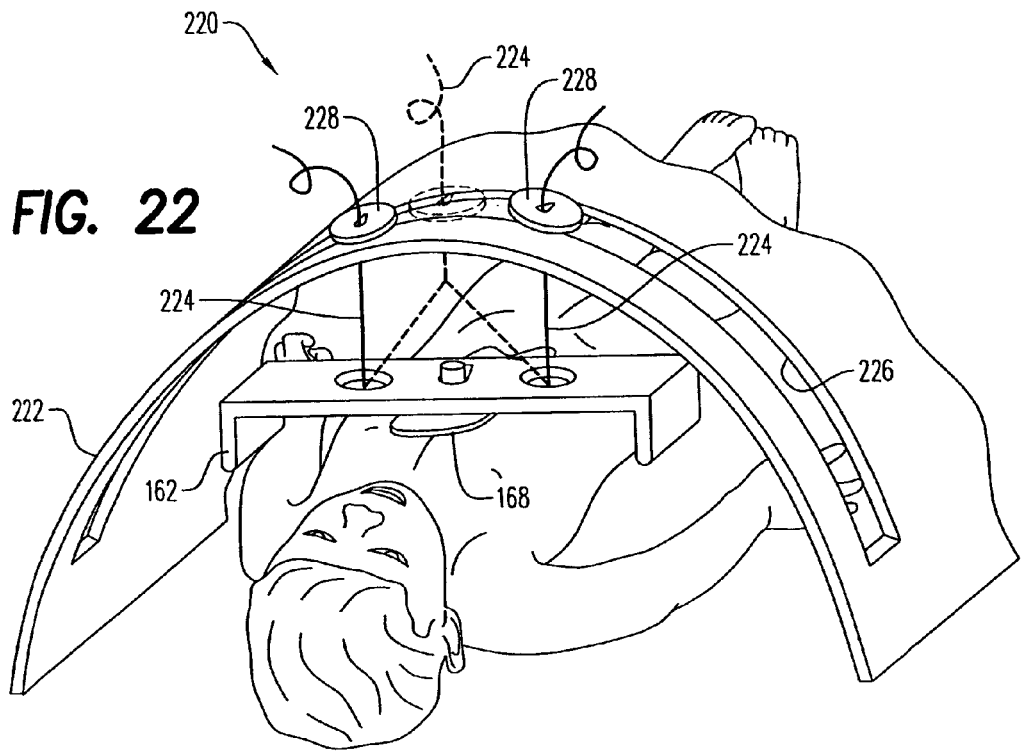
FIG. 22 is a perspective view showing an alternative technique for supporting the chest plate attached to a patient's chest.

An alternative technique for supporting chest plate 168 using anterior member 162 is illustrated in FIG. 22. Chest brace 220 in FIG. 22 includes a shield 222 under which the patient is located. Chest plate 168 and anterior member 126 are suspended from shield by a pair of suspension lines 224. This embodiment for the chest brace allows the patient to immediately receive a chest distending force, once chest plate 168 and anterior member 162 are attached to the patient, without having to place any structures behind the patient. This can be particularly important, for example, in a newborn infant whose chest is collapsing, where it is essential that the chest be prevented from collapsing as soon as possible with a minimal amount of handling of the infant. The ease of use of chest brace 220 allows the infant's chest to be immediately supported while avoiding lifting the baby. Shield 222 can also serve as a heat shield help keep the baby warm. Of course, other structures, such as a tripod or suspension arm, can be provide the function of shield 222, i.e., to suspend anterior member 162 and chest plate 168 above the patient and provide the chest distending force.

The present invention contemplates attaching suspension lines 224 to anterior member 162 in any suitable manner. Preferably, the suspension lines are attached to the anterior member in a manner that allows for secure attachment, while also allowing for easy removal of the suspension lines from the anterior member. For example, the present invention contemplates providing hooks at the end of the suspension lines that attach to a loop or other structure provided on the anterior member. Another variation of the present invention contemplates providing an attachment plate at the end of the suspension lines so that the suspension lines can be threaded through a hole in the anterior member with the attachment plate serving as a stopper to maintain the suspension line in an engaged relation with the anterior member.

Figure 24:
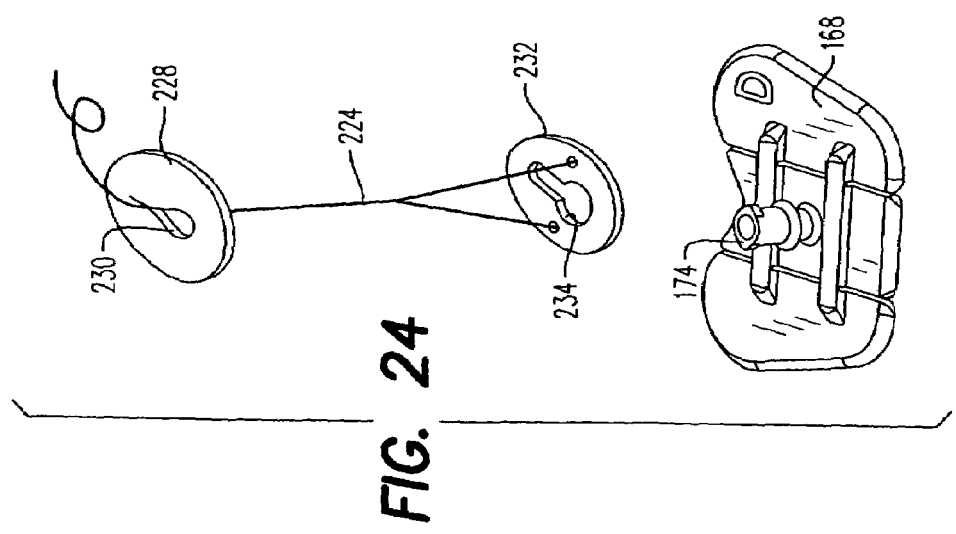
FIG. 24 is an exploded perspective view illustrating a technique for releaseably securing a suspension line to the chest plate in the embodiment shown in FIG. 23.

The present invention also contemplates attaching suspension lines 224 to shield 222 in any suitable manner. In the illustrated exemplary embodiment, shield 222 includes a slot 226 through which the suspension lines are threaded. The suspension lines are selectively engaged by means of clamping members 228 to suspend anterior member 162 and chest plate 168 above the patient to prevent chest wall collapse. Clamping member 228 can have any one of a variety of configurations so long at it performs the function of selectively securing the suspension lines to the shield. The illustrated embodiment of clamping member 228, which is shown in greater detail in FIG. 24, is a disk-shaped piece with a slot 230 defined therein. Slot 230 is shape so that suspension line 224 is pinched or clamped when the line is moved to one end of the slot.

Figure 23:
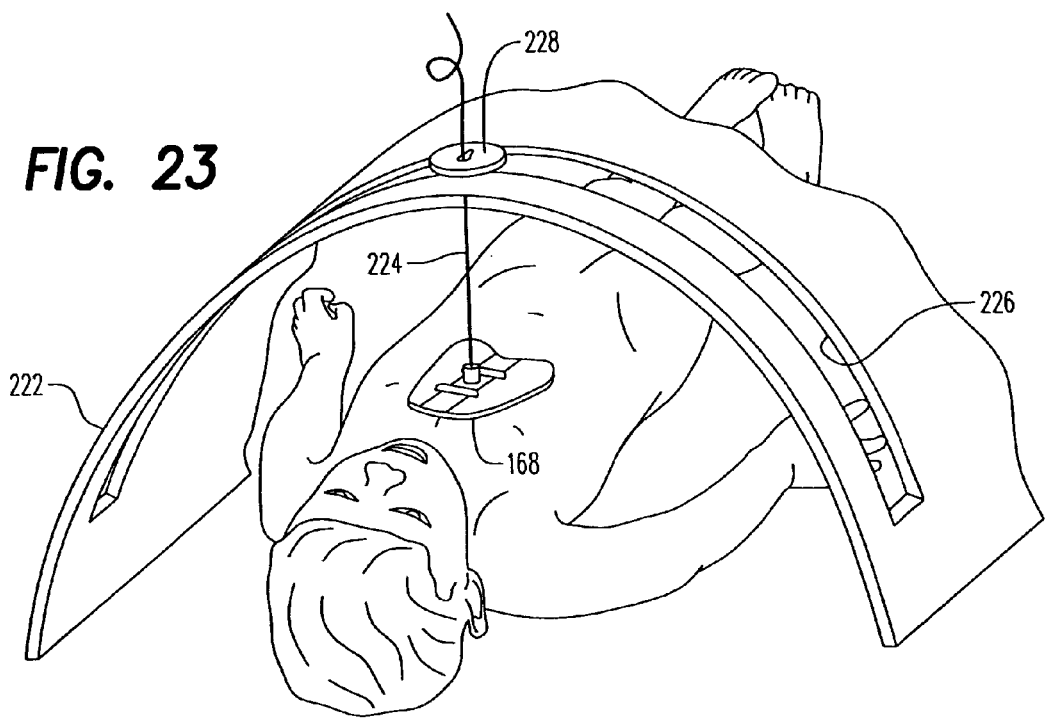
FIG. 23 is a perspective view showing a still further technique for supporting the chest plate attached to a patient's chest.

FIG. 23 illustrates a further technique for supporting chest plate 168 attached to the patient's chest. In this embodiment, shield 222 is again used to suspend the chest plate above the patient so that a distending force is applied to the patient's chest, preventing its collapse. However, in this embodiment, suspension line 224 is attached directly to chest plate 168, without using anterior member 168 as in FIG. 22. This embodiment of the present invention allows for even faster application of a distending force on a patient without having to handle the patient to attach a back plate or posterior member behind the patient and without attaching the anterior member.

In FIG. 23, suspension line 224 is directly attached to chest plate 168, for example, by being tied to stem 174. It is preferable, however, that suspension line 224 be releasably secured to the chest plate so that it can be easily and quickly removed so that the suspension system of FIGS. 22 and 23, which are contemplated as temporary or stopgap techniques for preventing chest wall collapse, can be replaced with a more stable chest brace system, such as those illustrated in FIGS. 15-18, 25 and 26.

FIG. 24 illustrates an exemplary technique for releasably securing suspension line 224 to chest plate 168. In this embodiment, suspension line 224 is attached to an attachment member 232 having a slot 234 defined therein. Slot 234 is sized and configured to receive stem 174 of chest plate 168 freely. Once stem 174 is inserted in a first portion of slot 234, the attachment member, stem, or both are moved so that the stem is located in a second portion of slot 234, where the stem is securely engaged with the attachment member. This technique is similar to the technique used to secure stems 174 and 186 to anterior member 162 and posterior member 164, respectively.

Figure 25:
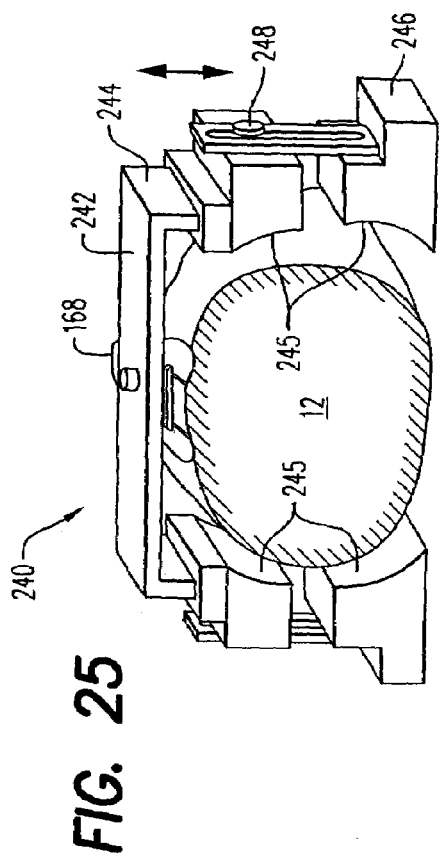
FIG. 25 is a perspective views illustrating an eighth embodiment of a chest brace according to the principles of the present invention.

FIG. 25 illustrates an eight embodiment of a chest brace 240 according to the principles of the present invention. Chest brace 240 is generally similar to chest brace 160 of FIGS. 15-18, except that in chest brace 240, there are no structural elements underlying the patient. Chest plate 168 is attached to an anterior member 242. The ends of anterior member 242 sit in trays 244 that are slideably attached to a base element 246 located on each side of the patient. Preferably, the interior surfaces 145 of the tray and base element are contoured to generally match the curvature of the patient. A locking mechanism 248, such as a screw, is provided to set the position of trays 244 relative to base element 246.

Figure 26:
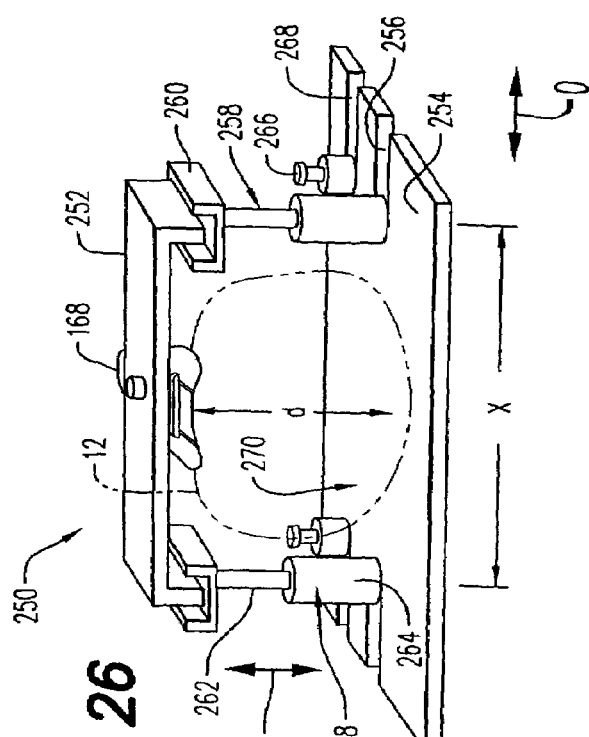
FIG. 26 is a perspective views illustrating a ninth embodiment of a chest brace according to the principles of the present invention.

FIG. 26 illustrates a ninth embodiment of a chest brace 250 according to the principles of the present invention. Chest brace 250 is also generally similar to chest brace 160 of FIGS. 15-18, except that chest brace 250 provides adjustability in lateral distance x between the sides of the brace, as indicated by arrow O, in addition to adjustability for the separation distance d between anterior member 252 and posterior member 254, as indicated by arrow P. Of course, different sized anterior members 252 may be necessary as different lateral distances x are selected. Alternatively, the length of anterior member 252 can also be adjustable using any conventional technique to match the selected lateral distance between the sides of the chest brace.

Adjusting lateral distance x is accomplished, for example, by providing a slot 256 in posterior member 254, in which an adjustable support member 258 is slideably located. Each adjustable support member includes a tray 260 for receiving an end of anterior member 252. The height of each support member 258 is adjustable, for example, by providing each support member with a first element 262 that is threaded into a second element 264, so that rotation of first element 262 relative to second element 264 alters the overall height of the support member.

The present invention contemplates a variety of techniques for locking support member 258 in position within slot 256, with only one example of such a technique being illustrated in FIG. 26. In this embodiment, a locking mechanism 266 is provided in a second slot 268 in posterior member 254 and is mechanically coupled to support member 258 for locking the support member in place. Locking mechanism 266 is any device that is capable of being selective secured to posterior member 254, such as a screw that can be tightened by hand.

Although posterior member 254 is illustrated as being planar, it is to be understood that exposed surface 270 can be contoured to approximate the shape of a patient's back, with the patient being adhere to surface 270 using any of the above described adhesive mechanisms. The present invention also contemplates providing a back plate that selectively secures to posterior member 254.

Figure 27:
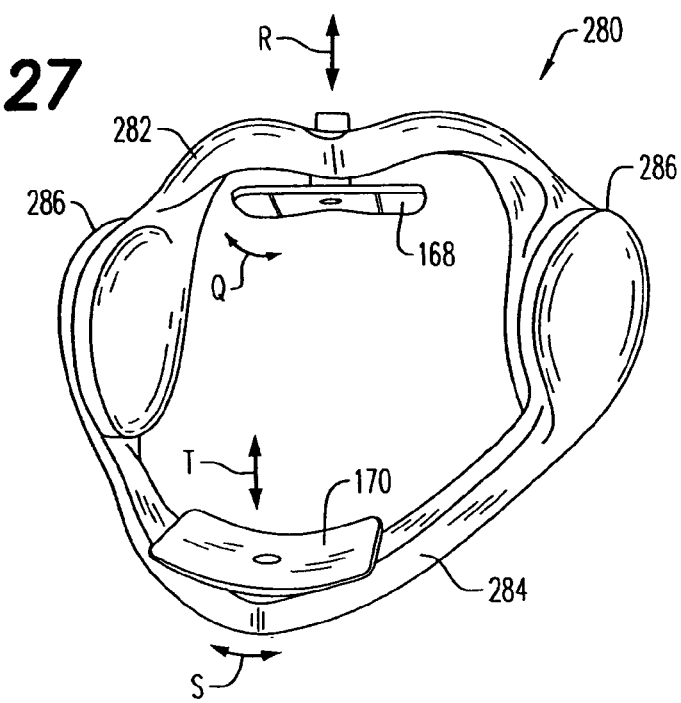
FIGS. 27, 28, and 29 are a front perspective, side perspective and front schematic views, respectively, illustrating a tenth embodiment of a chest brace according to the principles of the present invention.
Figure 28:
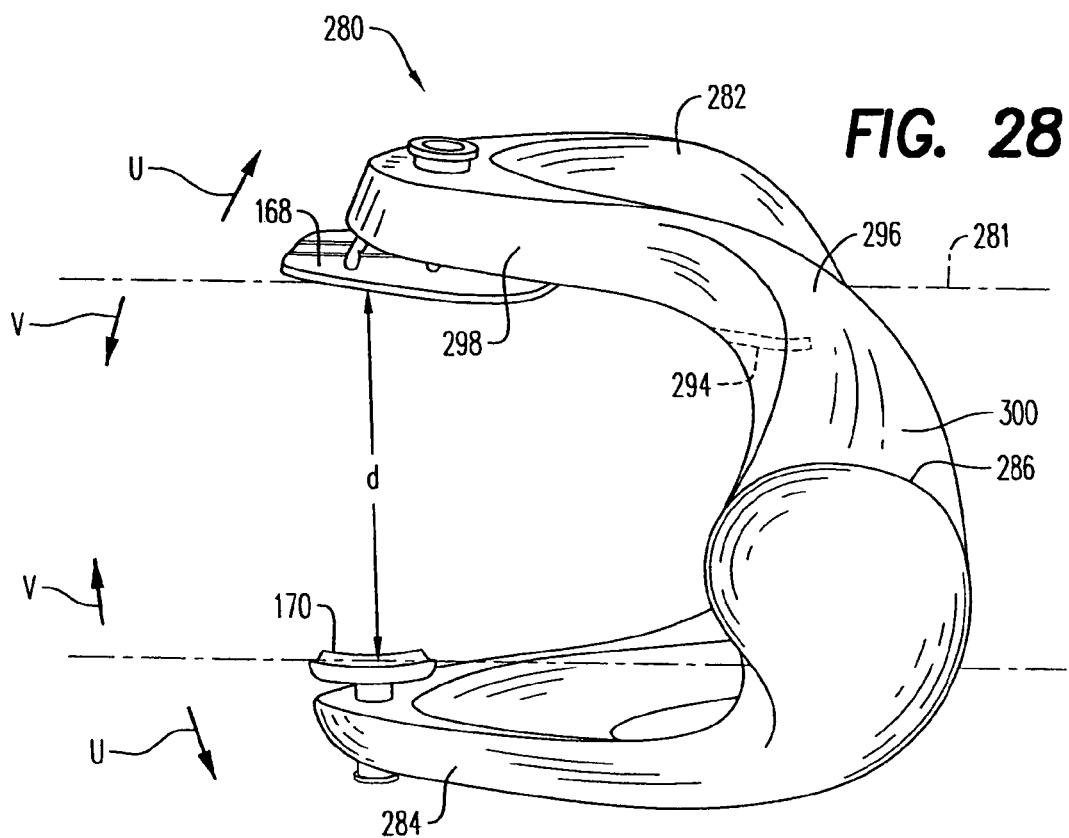
Figure 29:
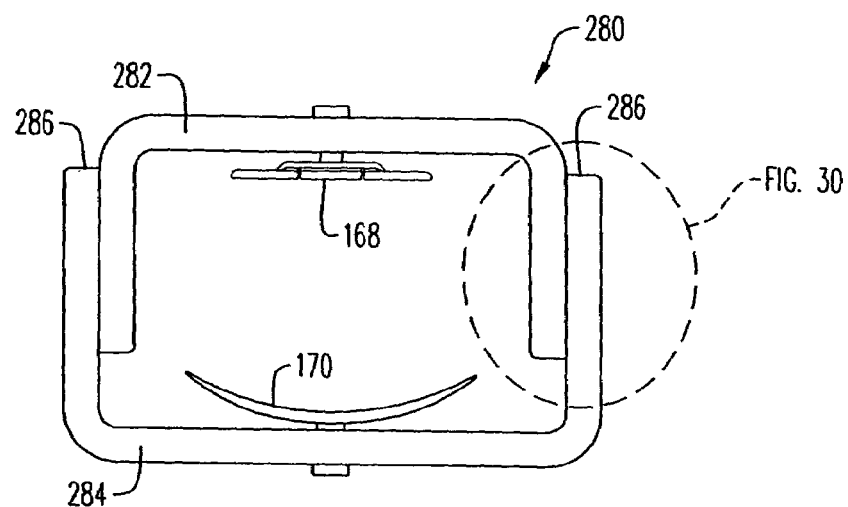

FIGS. 27, 28 and 29 illustrate a tenth embodiment of a chest brace 280 according to the principles of the present invention. Dashed line 281 in FIG. 28 represent the position of a patient wearing the chest brace. Chest brace 280 includes an anterior member 282 and a posterior member 284 coupled together at each end. As in the previous embodiments, the anterior and posterior members are preferably made from a plastic or semi-plastic material and are preferably transparent Anterior member 282 supports chest plate 168 and posterior member 284 supports back plate 170 in the same manner as the previous embodiments. That is, each chest or back plate is preferably selectively attachable to the associated anterior or posterior member, and, once attached, is either fixed to the respective anterior or posterior member, or moveably attached thereto. In a preferred embodiment, chest plate 168 is selectively attachable to anterior member 282 so at to be rotateable, as indicated by arrow Q, and moveable in an anterior-posterior direction indicated by arrow R. Back plate 170 is also preferably selectively attachable to posterior member 284 so at to be rotateable, as indicated by arrow S, and moveable in an anterior-posterior direction indicated by arrow T.

The ends of anterior member 282 and posterior member 284 define mechanical linkages 286 that couple these two members to one another. Mechanical linkages 286 preferably allow the anterior member to be physically detached from the posterior member so that they can be easily positioned about the patient and then reattached so that the anterior and posterior members provide the chest brace around the torso of the patient. Mechanical linkages also allow the anterior member and posterior member to open, as indicated by arrows U, and close, as indicated by arrows V, in a clam-shell like manner so that a distance d between the chest plate and the back plate can be controlled. See FIG. 28.

Figure 30:
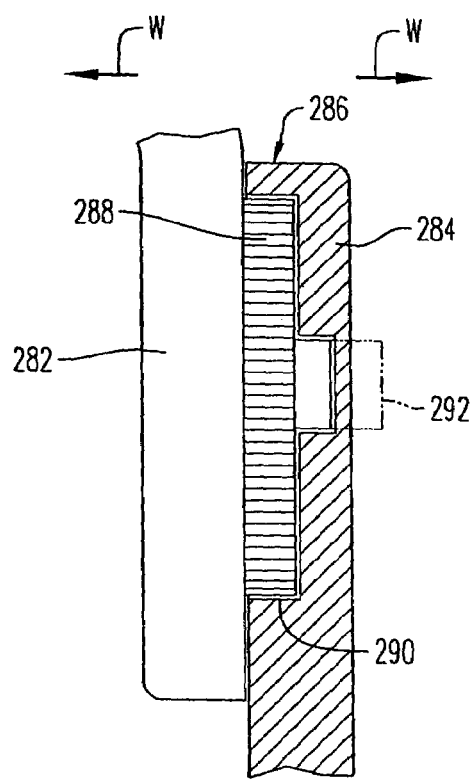
FIG. 30 is a detailed view, partially in section, of a mechanical linkage used in the chest brace of FIGS. 27-29.

FIG. 30 is a detailed view, partially in section, of an exemplary embodiment one of one mechanical linkage 286. In this embodiment, a circular array of teeth 288 are provided on anterior member 282. A corresponding array or teeth 290 are provided in posterior member 284. Teeth 288 and teeth 290 engage one another to prevent rotational movement of the anterior member relative to the posterior member. This allows distance d to be set. The flexibility of anterior member 282, posterior member 284, or both allows anterior member 282 to be bent away from posterior member 284, as indicated by arrow W, so that teeth 288 disengage from teeth 290. When disengaged, the anterior member is free to rotate relative to the posterior member to change distance d. Additional separation of anterior member 282 away from posterior member 284, as indicated by arrow W, allows these two members to completely detach from one another. The resiliency of the material or materials defining the anterior member, posterior member, or both maintains these two members in the engaged relation.

A wide variety of configurations are contemplated for mechanical linkages 286 to allow for the rotational movement of the anterior member relative to the posterior member. For example, teeth 288 or 290 can be shaped so that these two member rotateably move relative to one another in a ratchet-like fashion. The male-female relationship between the circular array of teeth and the cavity in which they are located in the anterior and posterior members can be reversed from that shown. The present invention also contemplates extending a protrusion, as indicated by dashed lines 292 in FIG. 30 beyond the sides of anterior member 284. Such a protrusion, when pressed, facilitates disengaging of teeth 288 and 290 by causing the anterior and posterior member to move apart. The present invention also contemplates providing a snap-fit or other technique for rotateably engaging the ends of the anterior member and posterior member in addition to or in place of relying on the resiliency of these members to maintain the ends in the engaged relation. As in the previous embodiments, this embodiment of the present invention also contemplates eliminating the chest plate, back plate, or both in favor of a direct attachment of the anterior member, posterior member, or both to the surface of the patient.

Anterior member 282 and posterior member 284 are configured and arranged such that the mechanical linkages are moved farther down the torso of the patient, i.e., in a direction away from the head, than in the previous embodiments. This arrangement provides a less cluttered area near the patient's upper body, which is typically where medical sensors are located. This arrangement also provides a relatively large amount of room for the patient's arms, while still providing the distending forces at the appropriate locations on the patient's thorax due to the curved or v-like shape of the anterior and posterior members. It can be appreciated that this arrangement for mechanical linkages 286 reduces the number or parts for such linkages between the anterior and posterior member as compared to the mechanical linkages of previous embodiments.

As noted above, the rotational position of anterior member 282 relative to posterior member 283, and, hence distance d, is controlled by at least one of the mechanical linkages. This sets the operating distance between the chest plate and the back plate. A small amount of additional distension of the chest is allowed for due to the translational movement of the chest plate and/or back plate in directions R and T, respectively, also due to the tolerances between teeth 288 and 290 in the mechanical linkages. However, the present invention contemplates providing even more freedom for distension of the chest in direction in direction U, while not allowing for any significant decrease in distance d between the chest and back plates.

This is accomplished according to one embodiment of the present invention by providing a channel, indicated by dashed lines 294, in each side of anterior member 282. Channel 294 effectively provides a hinge point in the anterior member, with the material at location 296 providing a bending moment that allows an upper portion 298 of anterior member 282 to move in direction U due the elasticity of this material while a lower portion 300 of anterior member 282 remains in the set position. Movement in direction V, that would decrease distance d, is prevented due to the engagement of the walls of channel 294 in much the same manner channels 180 in chest plate 168 prevent buckling of the chest plate when a load is applied.

It should be noted that the chest brace of the present invention is useful in doing more than preventing chest collapse occurring during respiration. In many situations, the shape of the patient's chest at rest is not within normal parameters, i.e., the patient's thoracic index is not in the normal range. In such cases, it is desirable to apply a distending force on the thorax to move chest walls to restore the thoracic index to acceptable parameters, even if the chest is not otherwise collapsing during respiration. For example, in an infant may have a malformed chest, applying a distending force on the chest, especially over an extended period of time, may allow the chest to grow in a proper manner without surgery. Maintaining the chest shape at its proper thoracic index, may not only improve the work of breathing, but may also serve to dilate blood vessels in the thorax to improve circulation.

Although the chest brace of the present invention has been described throughout as applying a distending force on the patient's chest in an anterior-posterior orientation, with minor structural changes, the chest brace of the present invention can be used to apply a distending force in a side-to-side orientation if desired. Also, it should be understood that the chest brace of the present invention can be used in adults as well as newborns, and can even have veterinary applications.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

Wwhat is claimed is:

1. A chest brace for a thorax of a patient comprising:
   (a) a rigid structure encircling the thorax of the patient and having a circumference, the rigid structure including:
      (1) an anterior member,
      (2) a posterior member, and
      (3) a linkage coupling the anterior member to the posterior member, wherein in an assembled configuration, the anterior member, the posterior member, and the linkage define the circumference for the rigid structure, wherein the linkage is moveable relative to the anterior member, the posterior member, or both to change a length of the circumference of the rigid structure, wherein the linkage maintains the anterior member a first distance from the posterior member during use of the chest brace over a plurality of respiratory cycles of the patient, allows expansion of such a patient's chest beyond the first distance by enabling the anterior member or the posterior member to move with the patient responsive to expansion of such a patient'chest beyond the first distance, and prevents the anterior member from moving closer than the first distance to the posterior member over the plurality of respiratory cycles, and wherein the first distance corresponds to a distance in which a chest of the patient is in a substantially non-collapsed position; and
   (b) a mechanism adapted to couple to a surface of the patient's chest to a portion of the rigid structure overlying the chest.

2. The chest brace according to claim 1, wherein the posterior member spans a back of the patient.

3. The chest brace according to claim 1, wherein the anterior member, the posterior member, or both are shaped to correspond, in general, to a shape of a surface of a portion of a human thorax.

4. The chest brace according to claim 1, wherein the mechanism is a hydrogel adhesive applied to a surface of the anterior member.

5. The chest brace according to claim 1, further comprising a chest plate operatively coupled to the anterior member and adapted to couple to a surface of a patient via the mechanism.

6. The chest brace according to claim 5, further comprising a stem extending from a surface of the chest plate, wherein the stem couples the chest plate to the anterior member.

* * * * *

UNITED STATES PATENT AND TRADEMARK OFFICE
CERTIFICATE OF CORRECTION

PATENT NO.        : 7,297,125 B2  
APPLICATION NO. : 11/128765  
DATED             : November 20, 2007  
INVENTOR(S)       : Charles Palmer et al.

Page 1 of 1

It is certified that error appears in the above-identified patent and that said Letters Patent is hereby corrected as shown below:

Title Page, Column 1, item 73

Line after "Trafford, PA (US) 15085" please add the following Heading and information regarding assignment:

--Assignees: The Penn State Research Foundation, University Park, PA (US); Respironics, Inc., Pittsburgh, PA (US)--

Signed and Sealed this

Twenty-third Day of June, 2009

JOHN DOLL  
*Acting Director of the United States Patent and Trademark Office*